(12) United States Patent
Enomura et al.

(10) Patent No.: US 10,208,208 B2
(45) Date of Patent: Feb. 19, 2019

(54) COMPOSITE PHTHALOCYANINE MICROPARTICLES AND METHOD FOR PRODUCING SAME

(71) Applicant: M. TECHNIQUE CO., LTD., Izumi-shi, Osaka (JP)

(72) Inventors: Masakazu Enomura, Izumi (JP); Daisuke Honda, Izumi (JP)

(73) Assignee: M. TECHNIQUE CO., LTD., Izumi-Shi, Osaka (JP)

( * ) Notice: Subject to any disclaimer, the term of this patent is extended or adjusted under 35 U.S.C. 154(b) by 0 days.

(21) Appl. No.: 15/535,966

(22) PCT Filed: Dec. 15, 2015

(86) PCT No.: PCT/JP2015/085096
§ 371 (c)(1),
(2) Date: Jun. 14, 2017

(87) PCT Pub. No.: WO2016/098777
PCT Pub. Date: Jun. 23, 2016

(65) Prior Publication Data
US 2017/0342272 A1  Nov. 30, 2017

(30) Foreign Application Priority Data

Dec. 15, 2014 (JP) ................. 2014-253490
Apr. 8, 2015 (JP) ................. 2015-079626

(51) Int. Cl.
| | |
|---|---|
| C07D 487/22 | (2006.01) |
| C09B 67/22 | (2006.01) |
| C09B 67/42 | (2006.01) |
| B01J 19/18 | (2006.01) |
| C07B 61/00 | (2006.01) |

(52) U.S. Cl.
CPC ....... C09B 67/0035 (2013.01); B01J 19/1887 (2013.01); C07D 487/22 (2013.01); C09B 67/0092 (2013.01); C07B 61/00 (2013.01)

(58) Field of Classification Search
CPC ................................................. C09B 67/0035
See application file for complete search history.

(56) References Cited

U.S. PATENT DOCUMENTS

| | | |
|---|---|---|
| 5,595,846 A | 1/1997 | Shigematsu et al. |
| 8,110,038 B2 | 2/2012 | Tanaka et al. |
| 2010/0155310 A1 | 6/2010 | Enomura |
| 2011/0023752 A1 | 2/2011 | Tanaka et al. |
| 2011/0177337 A1 | 7/2011 | Enomura |
| 2013/0071664 A1 | 3/2013 | Maekawa et al. |

FOREIGN PATENT DOCUMENTS

| | | |
|---|---|---|
| CN | 101981133 A | 2/2011 |
| EP | 0401782 A2 | 12/1990 |
| EP | 0401782 A3 | 12/1990 |
| EP | 2732871 A1 | 5/2014 |
| JP | 8-67829 A | 3/1996 |
| JP | 8-176458 A | 7/1996 |
| JP | 10-231439 A | 9/1998 |
| JP | 2002-155219 A | 5/2002 |
| JP | 2004-252443 A | 9/2004 |
| JP | 2008-239870 A | 10/2008 |
| JP | 2009-82902 A | 4/2009 |
| JP | 2012-12614 A | 1/2012 |
| JP | 2012-42536 A | 3/2012 |
| TW | 200918156 A | 5/2009 |
| WO | WO 2010/035861 A1 | 4/2010 |
| WO | WO 2011/152095 A1 | 12/2011 |
| WO | WO 2012/020715 A1 | 2/2012 |

OTHER PUBLICATIONS

International Search Report, issued in PCT/JP2015/085096, PCT/ISA/210, dated Mar. 15, 2016.
Extended European Search Report dated May 11, 2018 for corresponding European Application No. 15869982.7.

*Primary Examiner* — Brian E McDowell
(74) *Attorney, Agent, or Firm* — Birch, Stewart, Kolasch & Birch, LLP

(57) ABSTRACT

Composite phthalocyanine microparticles of a nano-order level, preferably on the order of 100 nm, that are optimal as a coloring material are provided; and a method for producing the same. The method for producing composite phthalocyanine microparticles includes a step (1) for preparing a dissolved solution by dissolving at least copper phthalocyanine and titanyl phthalocyanine and/or cobalt phthalocyanine as raw materials in a first solvent, a step (2) for precipitating composite phthalocyanine by mixing the dissolved solution obtained in step (1) with a second solvent that serves as a poor solvent of the abovementioned raw materials, and a step (3) for causing an organic solvent to act on the composite phthalocyanine obtained in step (2). Also provided are composite phthalocyanine microparticles containing at least copper phthalocyanine and titanyl phthalocyanine and/or cobalt phthalocyanine, the composite phthalocyanine microparticles having an aspect ratio of 1.1-2.5 and a particle size of 5-100 nm.

3 Claims, 27 Drawing Sheets

Fig. 24  Example 5-2 after step 2 (washing)

Fig. 25  Example 5-2 after step 2(washing)

Fig. 26 Example 5-2 after step 3(action)

COMPOSITE PHTHALOCYANINE MICROPARTICLES AND METHOD FOR PRODUCING SAME

TECHNICAL FIELD

The present invention relates to a composite phthalocyanine microparticle and a method for producing the said microparticle.

BACKGROUND ART

A copper phthalocyanine is a material widely used in the fields such as a pigment, a semiconductor, a photoreceptor, a recording medium, a solar cell, a liquid crystal, and a catalyst. Because the copper phthalocyanine has a clear hue, a high coloring power, and a fastness, it is used every field as a blue pigment.

In recent years, in order to further express or improve characteristics of the copper phthalocyanine, attempts have been made to produce a composite phthalocyanine added thereto with a phthalocyanine having a different metal.

In Patent Document 1, a blue pigment or paint composition comprising a cobalt phthalocyanine and a copper phthalocyanine is disclosed; and in Patent Document 2, a pigment composition for a color filter comprising an alpha-type cobalt phthalocyanine pigment and an epsilon-type copper phthalocyanine pigment is disclosed.

The copper phthalocyanine particles disclosed in Patent Document 1 and Patent Document 2 are produced by a crushing method. In order to improve the characteristics thereof, the particles are definitely required to be microparticles; however, with the crushing method, microparticles having the size of 100 nm or less, especially 50 nm or less, are difficult to be produced. Moreover, even if the microparticles as mentioned above could be produced, not only an enormous energy is required in the production thereof, but also a strong force is applied to the microparticles, resulting in poor crystallinity so that intended characteristics cannot be obtained. Therefore, in a recent trend of requiring a higher performance, there may be a limit in the crushing method.

On the other hand, as the one method to produce the copper phthalocyanine microparticle not having the drawbacks of the crushing method as mentioned above, a crystallization method by a poor solvent is known. In this method, the copper phthalocyanine microparticle is separated by mixing a raw material solution in which the copper phthalocyanine is dissolved in a good solvent being capable of dissolving the said compound with a poor solvent having a lower solubility to the same than the good solvent (Patent Document 3).

However, even in the crystallization method by a poor solvent, there still remains a problem that crystal growth of the copper phthalocyanine microparticle further takes place in an organic solvent. That is to say, because the copper phthalocyanine undergoes the crystal growth in an organic solvent, the microparticle becomes coarse so that the color characteristics are deteriorated.

In order to suppress the crystal growth, use of a crystal growth suppressor to the copper phthalocyanine may be contemplated. In Patent Document 4, a phthalocyanine having a different metal is suggested as the crystal growth suppressor. However, the method disclosed in Patent Document 4 is different from the crystallization method by a poor solvent as mentioned before. Therefore, in the case that the copper phthalocyanine is produced by the crystallization method by a poor solvent, there is no description with regard to in which process and with what procedure the phthalocyanine having a different metal is applied to the copper phthalocyanine so as to suppress the crystal growth.

For example, there is no description with regard to the ratio of the phthalocyanine having a different metal to the copper phthalocyanine. When the ratio of the phthalocyanine having a different metal to the copper phthalocyanine is high, the crystal growth can be suppressed, but the color characteristics are deteriorated due to the effect of the phthalocyanine having a different metal. On the other hand, when the ratio of the phthalocyanine having a different metal to the copper phthalocyanine is low, the crystal growth of the copper phthalocyanine microparticle cannot be suppressed, so that improvement of the color characteristics thereof cannot be expected. Patent Document 4 discloses no proposal with regard to the way how to solve these problems.

Meanwhile, as disclosed in Patent Document 5 and Patent Document 6, a micro reactor with a type of a forced thin film is known; in this reactor, a fluid is made to react in a thin film fluid formed between processing surfaces which are disposed in a position they are faced with each other so as to be able to approach to and separate from each other, at least one of which rotates relative to the other. The phthalocyanine microparticle produced by the micro reactor like this is finer and more homogeneous as compared with those produced by other conventional methods, so that, with this method, there are merits of further higher coloring strength and color development.

However, with this method on the contrary, the Ostwald ripening is facilitated thereby tending to cause increase in the size of the microparticle in the organic solvent and to cause necking. Accordingly, there is a dilemma that it is difficult for the copper phthalocyanine produced by the micro reactor thereby having finer and higher homogeneity to express the expected color characteristics.

In fact, the transmission/absorption spectra of the copper phthalocyanine microparticle of Patent Document 5 or Patent Document 6 in a visible light region has, in view of the absorption spectrum thereof, the highest peak near the wavelength of 600 nm and the second highest peak in the region of about 660 to 700 nm. In view of the transmission spectrum, the highest transmittance is in the region of 400 to 500 nm with the difference between the highest and lowest transmittance being 80% or more, whereas the transmittance increases again in the region of 620 to 800 nm. Therefore, the copper phthalocyanine has a reddish color in spite that it is expected to be a coloring material intrinsically having a blue to cyan color; and thus, improvement of the color characteristics in order to give a clearer blue color with eliminating the reddish color has been wanted.

In addition, especially in the case that the copper phthalocyanine was produced by using the micro reactor, the separation reaction took place rapidly; and thus, mere addition of the phthalocyanine having a different metal in the way as described in Patent Document 4 could not suppress the crystal growth of the separated microparticle, so that improvement of the color characteristics of the copper phthalocyanine could not be accomplished.

CITATION LIST

Patent Documents

Patent Document 1: Japanese Patent Laid-Open Publication No. H10-231439

Patent Document 2: Japanese Patent Laid-Open Publication No. 2004-252443

Patent Document 3: Japanese Patent Laid-Open Publication No. 2012-42536

Patent Document 4: Japanese Patent Laid-Open Publication No. 2002-155219

Patent Document 5: International Patent Laid-Open Publication No. 2010-035861

Patent Document 6: Japanese Patent Laid-Open Publication No. 2012-012614

SUMMARY OF THE INVENTION

Problems to be Solved by the Invention

With the background as mentioned above, the present invention has an object to provide: a composite phthalocyanine microparticle, with the size thereof being in a level of nanometers, preferably 100 nm or less, such as a copper-titanyl phthalocyanine microparticle, a copper-cobalt phthalocyanine microparticle, and a copper-titanyl-cobalt phthalocyanine microparticle, wherein the crystal growth thereof can be suppressed thereby satisfying the required characteristics so that it can be optimal as a coloring material such as a pigment etc.; and a method for producing the said composite phthalocyanine microparticle.

Means for Solving the Problems

Inventors of the present invention carried out an extensive investigation in order to solve the problems as mentioned above; and as a result, they found that the above-mentioned object could be accomplished by the composite phthalocyanine microparticle and the production method thereof as described below. On the basis of these findings, the present invention could be completed.

The present invention provides a method for producing a composite phthalocyanine microparticle comprising: step (1) in which as raw materials at least a copper phthalocyanine and a titanyl phthalocyanine and/or a cobalt phthalocyanine are dissolved in a first solvent to obtain a dissolved solution; step (2) in which the dissolved solution obtained in the step (1) is mixed with a second solvent capable of being a poor solvent to the raw materials to effect separation of a composite phthalocyanine; and step (3) in which an organic solvent is made to act on the composite phthalocyanine obtained in the step (2).

In the present invention, the organic solvent is preferably a solvent based on an aromatic compound or a solvent based on a heterocyclic compound; and for example, the organic solvent is preferably at least one solvent selected from the group consisting of styrene, xylene, toluene, benzene, cresol, cumene, tetrahydrofuran, and pyridine. When the solvent based on an aromatic compound or on a heterocyclic compound that can induce or facilitate the crystal transformation from an alpha-type copper phthalocyanine to a beta-type crystal structure or the like which is usually more stable than the alpha-type is used as the organic solvent, surprisingly the crystal transformation to the more stable beta-type crystal structure or the like can be suppressed; and on top of it, the crystal growth can be suppressed.

Also, the present invention may be executed such that a mixing weight ratio of the raw materials (copper phthalocyanine/titanyl phthalocyanine and/or copper phthalocyanine/cobalt phthalocyanine) in the step (1) is in a range of 1 or more to less than 20.

Further, the present invention may be executed such that the titanyl phthalocyanine and the cobalt phthalocyanine are simultaneously or successively dissolved in the step (1).

At least the step (2) may be executed in a micro reactor in which at least two fluids to be processed are made to react with each other, and of the fluids to be processed, at least one fluid to be processed is the dissolved solution, and the other fluid to be processed is the second solvent. Specifically, at least the step (2) may be executed by using a micro reactor in which at least two fluids to be processed are introduced into between a first processing surface and a second processing surface which are disposed in a position they are faced with each other so as to be able to approach to and separate from each other, at least one of which rotates relative to the other; a separating force which acts in a direction to separate the first processing surface and the second processing surface from each other is generated by an introduction pressure imparted to between the first processing surface and the second processing surface; with keeping a minute distance between the first processing surface and the second processing surface by the separating force, the at least two fluids to be processed are caused to converge with each other between the first processing surface and the second processing surface that are kept at the minute distance thereby causing to pass the fluids to be processed through between the first processing surface and the second processing surface so as to form a thin film fluid; and the fluids to be processed are made to react with each other in the thin film fluid. In this embodiment, of the fluids to be processed, at least one fluid to be processed may be the dissolved solution and the other fluid to be processed may be the second solvent.

Also, the present invention may be executed such that both the composite phthalocyanine obtained in the step (2) and the composite phthalocyanine obtained in the step (3) are of the same crystal type. That is to say, this indicates that even if the organic solvent is made to act on the composite phthalocyanine obtained in the step (2), the crystal transformation does not take place in the step (3).

Also, in the present invention, a surfactant or a dispersant may be added in the organic solvent.

In addition, the present invention provides the composite phthalocyanine microparticle wherein the composite phthalocyanine microparticle comprises at least the copper phthalocyanine and the titanyl phthalocyanine and/or the cobalt phthalocyanine, the said microparticle having an aspect ratio in a range of 1.1 to 2.5 (both inclusive) and a particle diameter in a range of 5 to 100 nm (both inclusive).

In the present invention, the aspect ratio is defined as the ratio of a long side to a short side in each composite phthalocyanine microparticle such as the copper-titanyl phthalocyanine microparticle etc. For example, if the shape thereof can be regarded as a cuboid shape or a quasi-cuboid shape, this is defined as the ratio of the longest side to the shortest side of the three sides thereof. If the shape thereof can be regarded as a sphere shape or a quasi-sphere shape, this is defined as the ratio of the longest diameter to the shortest diameter. Also, for example, the aspect ratio is defined as an average value of the long diameters to the short diameters of 100 particles measured with an observation by using a transmission electron microscopy (TEM).

In the present invention, the particle diameter is defined as an average diameter of 100 particles measured with an observation by using a transmission electron microscopy (TEM).

The present invention may be executed such that a relative value ([Abs(a)]/[Abs(b)]) is 0.8 or more, wherein Abs (a) is defined as "Abs" at the peak top in the range of 655 to 700 nm of an absorption spectrum of the composite phthalocyanine microparticle in a UV-visible region and Abs (b) is defined as "Abs" at the peak top in the range of 550 to 640 nm of the same.

In the present invention, the above-mentioned "Abs" is defined as the absorbance measured in the UV-visible absorption spectrum and calculated on the basis of the Lambert-Beer's law; and "Abs" at the peak top is defined as the maximum value among "Abs" in a specified wavelength range.

Advantageous Effects of Invention

By using the method of the present invention for producing a composite phthalocyanine microparticle, the composite phthalocyanine microparticle with the size thereof in a level of nanometers, preferably 100 nm or less, thereby being optimal as a coloring material, can be obtained. Especially, by using the production method of the present invention, the crystal growth that takes place in a certain solvent can be suppressed. In addition, by using the method of the present invention for producing a composite phthalocyanine microparticle, not only the solvent resistance thereof can be enhanced but also the crystal growth of the same can be suppressed even in an organic solvent that can facilitate the crystal growth; and thus, the intrinsic characteristics of the copper phthalocyanine microparticle can be expressed.

In addition, because the composite phthalocyanine microparticle of the present invention has the properties such as the above-mentioned aspect ratio and particle diameter, scattering of the light can be suppressed; and thus, this is optimal especially as the coloring material having a clear blue color.

(A) shows a rough cross-sectional view of the micro reactor used for execution of the fluid processing method according to embodiments of the present invention; (B) shows a rough cross-sectional view of the micro reactor used for execution of the fluid processing method according to other embodiments of the present invention.

FIG. 2

Figure 1:
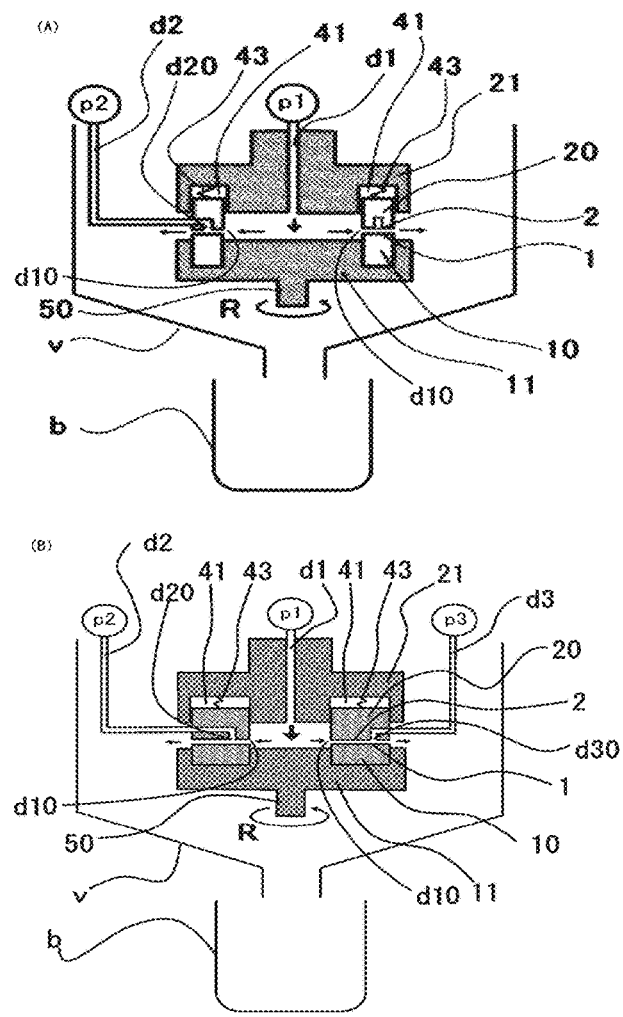
FIG. 1

This shows an enlarged view of the essential part of the processing surface shown in FIG. 1 (A) and FIG. 1 (B).

FIG. 3

These are measurement results of the absorption spectra of the copper-titanyl phthalocyanine microparticles etc. produced in Example 1.

FIG. 4

These are measurement results of the absorption spectra of the copper-titanyl phthalocyanine microparticles produced in Example 1 and Example 2.

FIG. 5

These are measurement results of the transmission spectra of the copper-titanyl phthalocyanine microparticles etc. produced in Example 1.

FIG. 6

These are measurement results of the transmission spectra of the copper-titanyl phthalocyanine microparticles produced in Example 1 and Example 2.

FIG. 7

This is the picture of the copper-titanyl phthalocyanine microparticles produced in Example 1 observed with a transmission electron microscope (TEM) (observation magnification of 50000).

FIG. 8

This is the picture of the copper-titanyl phthalocyanine microparticles of the present invention produced in Example 1 observed with a transmission electron microscope (TEM) (observation magnification of 10000).

FIG. 9

This is the picture of the copper-titanyl phthalocyanine microparticles produced in Comparative Example 1-2 observed with a transmission electron microscope (TEM) (observation magnification of 50000).

FIG. 10

This is the picture of the copper-titanyl phthalocyanine microparticles produced in Comparative Example 1-2 observed with a transmission electron microscope (TEM) (observation magnification of 10000).

FIG. 11

These are the measurement results of the absorption spectra of the copper-cobalt phthalocyanine microparticles or the copper-titanyl-cobalt phthalocyanine microparticles produced in Examples 3-1 to 3-5 and Comparative Examples 3-1 to 3-5.

FIG. 12

These are the measurement results of the transmission spectra of the copper-cobalt phthalocyanine microparticles or the copper-titanyl-cobalt phthalocyanine microparticles produced in Examples 3-1 to 3-5 and Comparative Examples 3-1 to 3-5.

FIG. 13

These are the XRD measurement results of the copper-titanyl phthalocyanine microparticles etc. produced in Example 1.

FIG. 14

These are the XRD measurement results of the copper-cobalt phthalocyanine microparticles or the copper-titanyl-cobalt phthalocyanine microparticles produced in Comparative Examples 3-1 to 3-5.

FIG. 15

These are the XRD measurement results of the copper-cobalt phthalocyanine microparticles or the copper-titanyl-cobalt phthalocyanine microparticles produced in Examples 3-1 to 3-5.

FIG. 16

These are the measurement results of the absorption spectra of the copper-cobalt phthalocyanine microparticles produced in Examples 3-1 and 3-1-1 to 3-1-3 and Comparative Example 3-1.

FIG. 17

These are the measurement results of the absorption spectra of the copper-titanyl-cobalt phthalocyanine microparticles produced in Examples 3-2 and 3-2-1 to 3-2-2 and Comparative Example 3-2.

FIG. 18

These are the measurement results of the absorption spectra of the copper-titanyl-cobalt phthalocyanine microparticles produced in Examples 3-3 and 3-3-1 and Comparative Example 3-3.

FIG. 19

These are the measurement results of the absorption spectra of the copper-titanyl phthalocyanine microparticles etc. produced in Example 2.

FIG. 20

These are the measurement results of the transmission spectra of the copper-titanyl phthalocyanine microparticles etc. produced in Example 2.

FIG. 21

These are the measurement results of the absorption spectra of the copper-titanyl-cobalt phthalocyanine microparticles produced in Examples 4-1-1 to 4-1-4 and Comparative Example 4-1.

FIG. 22

These are the measurement results of the absorption spectra of the copper-titanyl-cobalt phthalocyanine microparticles produced in Examples 4-2-1 to 4-2-4 and Comparative Example 4-2.

FIG. 23

This shows an example of the production procedure in Examples 5 to 8 of the present invention.

FIG. 24

This is the picture of the composite phthalocyanine microparticles of the present invention obtained after the step 2 (washing step) of Example 5-2, observed with a transmission electron microscope (TEM).

FIG. 25

This is the picture of the composite phthalocyanine microparticles of the present invention obtained after the step 2 (washing step) of Example 5-2, observed with a transmission electron microscope (TEM).

FIG. 26

This is the picture of the composite phthalocyanine microparticles of the present invention obtained after the step 3 (action step) of Example 5-2, observed with a transmission electron microscope (TEM).

FIG. 27

This is the picture of the composite phthalocyanine microparticles of the present invention obtained after the step 3 (action step) of Example 5-2, observed with a transmission electron microscope (TEM).

DESCRIPTION OF THE EMBODIMENTS

Hereinafter, embodiments of the present invention will be explained in detail.

The method of the present invention for producing a phthalocyanine microparticle comprises:

step (1) in which as raw materials at least a copper phthalocyanine and a titanyl phthalocyanine and/or a cobalt phthalocyanine are dissolved in a first solvent to obtain a dissolved solution;

step (2) in which the dissolved solution obtained in the step (1) is mixed with a second solvent capable of being a poor solvent to the raw materials to effect separation of a composite phthalocyanine microparticle; and step (3) in which an organic solvent is made to act on the composite phthalocyanine microparticle obtained in the step (2).

The composite phthalocyanine microparticle according to the present invention has the size of in a level of nanometers, preferably 100 nm or less; however, depending on the use thereof, the size may be, for example, in the range of 1 to 200 nm, or in the range of 2 to 80 nm, or in the range of 5 to 50 nm, or in the range of 10 to 30 nm. For example, by using the production method of the present invention, the microparticle having the size in the above-mentioned range can be efficiently obtained.

The production method of the present invention comprises the step (1) in which as raw materials at least a copper phthalocyanine and a titanyl phthalocyanine and/or a cobalt phthalocyanine are dissolved in a first solvent to obtain a dissolved solution. Here, it should be noted that the first solvent is the solvent capable of being a good solvent to the raw materials.

In the present invention, the first solvent to be used in the step (1) is preferably a solvent capable of being a good solvent to the copper phthalocyanine and/or the titanyl phthalocyanine, or a solvent capable of being a good solvent to the copper phthalocyanine and/or the cobalt phthalocyanine.

There is no particular restriction with regard to the first solvent; and illustrative example of the solvent usable therein includes, in the case of an acidic solution, sulfuric acid, hydrochloric acid, nitric acid, trifluoroacetic acid, phosphoric acid, methanesulfonic acid, dodecylbenzenesulfonic acid, and trichloroacetic acid. Especially when the surface-treated copper-titanyl phthalocyanine microparticle or the like is produced, fuming sulfuric acid, chlorosulfuric acid, fuming nitric acid, or the like is preferable. Besides, as for the good solvent, those which can be used include: amide solvents such as 1-methyl-2-pyrrolidinone, 1,3-dimethyl-2-imidazolidinone, 2-pyrrolidinone, ε-caprolactam, formamide, N-methylformamide, N,N-dimethylformamide, acetamide, N-methylacetamide, N,N-dimethylacetamide, N-methylpropaneamide, and hexamethyl phosphoric triamide; dimethyl sulfoxide; and a mixture of them. Moreover, in addition to the above-mentioned, an embodiment using the dissolved solution that the copper phthalocyanine and the titanyl phthalocyanine are dissolved into a solution obtained by adding a basic or an acidic substance into various organic solvents may also be employed. Illustrative example of the basic substance to be added into the organic solvent includes sodium hydroxide, potassium hydroxide, sodium methoxide, and sodium ethoxide. Illustrative example of the acidic substance to be added, similarly to those described above, includes sulfuric acid, hydrochloric acid, nitric acid, trifluoroacetic acid, phosphoric acid, methanesulfonic acid, dodecylbenzenesulfonic acid, trichloroacetic acid, and chlorosulfuric acid. These substances may be used singly or as a mixture of two or more of them.

In the case that the copper phthalocyanine, the titanyl phthalocyanine, and the cobalt phthalocyanine are used as the raw materials, a solvent capable of being a good solvent to at least one phthalocyanine among the three phthalocyanines may be used as the first solvent, while a solvent capable of being a good solvent to all the three phthalocyanines is preferable.

In the step (1), the dissolved solution that the copper phthalocyanine and the titanyl phthalocyanine or the cobalt phthalocyanine are dissolved into the first solvent (the copper phthalocyanine/titanyl phthalocyanine solution or the copper phthalocyanine/cobalt phthalocyanine solution) may be prepared by dissolving the copper phthalocyanine and the titanyl phthalocyanine or the cobalt phthalocyanine into the foregoing good solvent simultaneously; or alternatively, the dissolved solution may be prepared by dissolving each of the copper phthalocyanine and the titanyl phthalocyanine or the cobalt phthalocyanine into the good solvent or the like followed by mixing the respective resulting solutions as appropriately.

In the present invention, there is no particular restriction with regard to the copper phthalocyanine, the titanyl phthalocyanine, and the cobalt phthalocyanine to be used in the copper phthalocyanine/titanyl phthalocyanine solution and the copper phthalocyanine/cobalt phthalocyanine solution; and thus, any publicly known compounds of them may be used.

In the present invention, the weight ratio of the mixture of the copper phthalocyanine and the titanyl phthalocyanine (copper phthalocyanine/titanyl phthalocyanine) in the step (1) is preferably in the range of 1 or more to less than 20, while the ratio may be in the range of 1.5 or more to less than 9.0, or in the range of 2.0 or more to less than 6.0, or in the range of 2.5 or more to less than 4.0. When the ratio is within the above-mentioned range, a clear blue color can be ensured more surely.

Also, in the present invention, the weight ratio of the mixture of the copper phthalocyanine and the cobalt phthalocyanine (copper phthalocyanine/cobalt phthalocyanine) in the step (1) is preferably in the range of 1 or more to less than 20, while the ratio may be in the range of 1.5 or more to less than 9.0, or in the range of 2.0 or more to less than 6.0, or in the range of 2.5 or more to less than 4.0. When the ratio is within the above-mentioned range, a clear blue color can be ensured more surely.

Also, in the method of the present invention for producing a composite phthalocyanine microparticle, in the step (1), the titanyl phthalocyanine and the cobalt phthalocyanine may be dissolved simultaneously or successively. With the embodiment mentioned above, the titanyl phthalocyanine and the cobalt phthalocyanine, besides the copper phthalocyanine, are contained in the dissolved solution obtained in the step (1), thereby the copper-titanyl-cobalt phthalocyanine, i.e., the composite phthalocyanine microparticle obtained therein, can express the foregoing effects similarly to the foregoing microparticle. Meanwhile, the term "successively" includes any order of dissolution among the copper phthalocyanine, the titanyl phthalocyanine, and the cobalt phthalocyanine; or alternatively, after each of two or three dissolved solutions is prepared, these solutions may be mixed as appropriately.

Also, in the present invention, the weight ratio of the mixture of the copper phthalocyanine, the titanyl phthalocyanine, and the cobalt phthalocyanine in the step (1) (copperphthalocyanine:titanylphthalocyanine:cobaltphthalocyanine) may be, for example, 60:30:10, or 60:20:20, or 65:30:5; or alternatively, the ratio may be 70:30:0 or 70:0:30; or even the ratio may be 80:5:15, or 85:15:0, or 85:0:15, or 90:5:5, or 95:5:0, or 95:0:5. With the embodiments mentioned above, the composite phthalocyanine microparticle having intended particle diameter, particle shape, or characteristics such as color characteristics can be selectively produced in accordance with the purpose thereof.

Step (1) is the step to prepare the dissolved solution by dissolving or molecular-dispersing at least the copper phthalocyanine and the titanyl phthalocyanine and/or the cobalt phthalocyanine into the first solvent. Step (1) is executed preferably by using a high speed agitator with the peripheral speed of an agitation blade thereof being 1 m/s or more. With this, as a matter of course, generation of coarse particles due to the substances not yet dissolved in the dissolved solution can be suppressed; in addition, even when two or more molecules or elements are dissolved, the dissolved solution in a more homogeneously dissolved state can be prepared promptly. Therefore, even in the case that the composite phthalocyanine microparticle was separated by mixing the dissolved solution with the second solvent capable of being a poor solvent to the raw materials in a thin film fluid formed between at least two processing surfaces which are disposed in a position they are faced with each other so as to be able to approach to and separate from each other, at least one of which rotates relative to the other, a more uniform and homogeneous microparticle than ever could be prepared.

The method for the high speed agitation is not particularly restricted; the agitation may be conducted with the agitating or dissolving machines such as those using various shearing methods, a friction method, a high pressure jet method, and an ultrasonic method, as well as an emulsifier; a disperser; and a homogenizer. Illustrative example thereof includes continuous emulsifiers such as Ultra Turrax (manufactured by IKA Corp.), Polytron (manufactured by KINEMATICA AG), TK Homomixer (manufactured by PRIMIX Corp.), Ebara Milder (manufactured by EBARA Corp.), TK Homomic Line Flow (manufactured by PRIMIX Corp.), Colloid Mill (manufactured by Shinko Pantech Co., Ltd.), Slusher (manufactured by Nippon Coke & Engineering Co., Ltd.), Trigonal Wet-Type Fine Grinding Mill (manufactured by Mitsui Miike Machinery Co., Ltd.), Cavitron (manufactured by Eurotech Co., Ltd.), and Fine Flow Mill (manufactured by Pacific Machinery & Engineering Co., Ltd.); and the batch emulsifier or both the batch and continuous emulsifier such as Clearmix (manufactured by M. Technique Co., Ltd.), Clearmix Dissolver (manufactured by M. Technique Co., Ltd.), and Filmix (manufactured by PRIMIX Corp.). In addition, an ultrasonic homogenizer or an ultrasonic cleaning machine may also be used.

Also, the production method of the present invention has the step (2) in which the dissolved solution obtained in the step (1) is mixed with a second solvent capable of being a poorer solvent to the raw materials than the dissolved solution to effect separation of the composite phthalocyanine. Here, it should be noted that the second solvent being capable of a poor solvent to the raw materials is the solvent capable of being a poor solvent whose solubility to the raw materials is lower than the first solvent.

Meanwhile, the composite phthalocyanine that is separated by mixing the dissolved solution with the second solvent includes a precursor to the composite phthalocyanine microparticle of the present invention.

The second solvent capable of being a poor solvent to the raw materials in the step (2) is preferably a solvent capable of being a poorer solvent to the copper phthalocyanine and/or the titanyl phthalocyanine than the first solvent, or a solvent capable of being a poorer solvent to the copper phthalocyanine and/or the cobalt phthalocyanine than the first solvent. There is no particular restriction with regard to the second solvent capable of being a poorer solvent to the raw materials than the first solvent; and an embodiment can be executed by using the solvent that has a lower solubility to the copper phthalocyanine and the titanyl phthalocyanine (or the cobalt phthalocyanine) rather than the solvent that dissolved copper phthalocyanine and the titanyl phthalocyanine (or the cobalt phthalocyanine). Illustrative example thereof includes water, alcohol compound solvents, amide compound solvents, ketone compound solvents, ether compound solvents, aromatic compound solvents, carbon disulfide, aliphatic compound solvents, nitrile compound solvents, sulfoxide compound solvents, halogen compound solvents, ester compound solvents, ionic liquid solvents, carboxylic acid compound solvents, sulfonic acid compound solvents, and sulfolane compound solvents. These solvents may be used singly or as a mixture of two or more of them. Meanwhile, in the present invention, the solvent capable of being a poor solvent is preferably the solvent whose solubility to the copper phthalocyanine and the titanyl phthalocyanine and/or the cobalt phthalocyanine is 0.01% or less by mass. In the case of the second solvent, too, when plural components are mixed or dissolved therein, it is preferable that the preparation procedure be conducted with the before-mentioned high speed agitation.

The fluid containing the dissolved solution, or the fluid containing the second solvent capable of being a poor solvent to the raw materials, or the both fluids may contain a block copolymer, a high-molecular weight polymer, a surfactant, or a dispersant other than these substances. Further, the foregoing dispersant may be included in a third fluid which is different from both the fluid containing the dissolved solution and the fluid containing the second solvent capable of being a poor solvent to the raw materials.

As for the surfactant and the dispersant, various commercially available products for use in dispersing pigments can be used. Illustrative example of the surfactant and dispersant includes those based on dodecylbenzenesulfonic acid such as sodium dodecyl sulfonate and Neogen R-K (manufactured by Dai-Ichi Kogyo Seiyaku Co., Ltd.); Solsperse 20000, Solsperse 24000, Solsperse 26000, Solsperse 27000, Solsperse 28000, and Solsperse 41090 (all manufactured by Avecia Corp.); Disperbyk 160, Disperbyk 161, Disperbyk 162, Disperbyk 163, Disperbyk 166, Disperbyk 170, Disperbyk 180, Disperbyk 181, Disperbyk 182, Disperbyk 183, Disperbyk 184, Disperbyk 190, Disperbyk 191, Disperbyk 192, Disperbyk 2000, and Disperbyk 2001 (all manufactured by BYK-Chemie); Polymer 100, Polymer 120, Polymer 150, Polymer 400, Polymer 401, Polymer 402, Polymer 403, Polymer 450, Polymer 451, Polymer 452, Polymer 453, EFKA-46, EFKA-47, EFKA-48, EFKA-49, EFKA-1501, EFKA-1502, EFKA-4540, and EFKA-4550 (all manufactured by EFKA Chemical Corp.); Flowlen DOPA-158, Flowlen DOPA-22, Flowlen DOPA-17, FlowlenG-700, FlowlenTG-720W, Flowlen-730W, Flowlen-740W, and Flowlen-745W (all manufactured by Kyoeisha Chemical Co., Ltd.); Ajisper PA111, Ajisper PB711, Ajisper PB811, Ajisper PB821, and Ajisper PW911 (all manufactured by Ajinomoto Co., Inc.); Johncryl 678, Johncryl 679, and Johncryl 62 (all manufactured by Johnson Polymer B.V.); and Aqualon KH-10 and Hightenol NF-13 (both manufactured by Dai-Ichi Kogyo Seiyaku Co., Ltd.). These may be used singly or as a mixture of two or more of them.

Hereinafter, explanation will be made with regard to the case that surface treatment is conducted on the above-mentioned composite phthalocyanine.

Surface treatment of the composite phthalocyanine by way of introducing a modification group onto at least the surface thereof may be conducted, for example in the case of using the micro reactor as described in FIG. 1, by including a surface-modifying agent in the fluid to be introduced into between the processing surfaces 1 and 2. The surface-modifying agent may be included in any one of the fluid containing the dissolved solution (first fluid) and the fluid containing the second solvent capable of being a poor solvent to the raw materials (second fluid) or in both of them, or alternatively, the surface-modifying agent may be included in a third fluid which is different from both the fluid containing the dissolved solution and the fluid containing the second solvent capable of being a poor solvent to the raw materials. A combination of the first fluid and the second fluid is not limited especially to the above embodiment.

The modification group used as the surface-modification group to be introduced onto at least pigment's surface is not particularly limited in its kind. When the surface treatment aims at improvement of the dispersibility, the modification group may be selected in accordance with, for example, a solvent and a dispersant intending to disperse. Illustrative example thereof includes polar groups such as an acidic group and a basic group; a salt structure of each of the said polar groups, a structure with high polarizability in which a highly polar atom such as oxygen and sulfur and/or an aromatic ring or the like are introduced, and a modifying group having a hydrogen bonding group, a hetero ring, an aromatic ring, or the like. Illustrative example of the acidic group includes a hydroxy group (hydroxyl group), a sulfonic group (sulfo group), a carboxylic acid group, a phosphoric group, and a boric acid group. Illustrative example of the basic group includes an amino group. Illustrative example of the hydrogen bonding group includes a urethane moiety, a thiourethane moiety, a urea moiety, and a thiourea moiety.

When the surface treatment aims at other than improvement of the dispersibility, for example, in the case that surface of the composite phthalocyanine is to be made water-repellent, lipophilic, or compatible with an organic solvent, a surface-modifying agent containing a lipophilic functional group is contained in any one of the first fluid and the second fluid or both, and then surface of the composite phthalocyanine discharged from between the processing surfaces 1 and 2 is made lipophilic by way of introduction of the lipophilic functional group as the modification group, so that the surface treatment to make the surface lipophilic may be achieved. The surface-modifying agent may be contained in a third fluid which is different from both the first fluid and the second fluid.

In the case that surface of the composite phthalocyanine is subjected to the treatment of attaching a resin as the surface-modifying agent, a material containing the resin is contained in any one of the first fluid and the second fluid or both, and then surface of the composite phthalocyanine discharged from between the processing surfaces 1 and 2 are at least partly covered with the resin, so that the surface treatment to make the surface, for example, hydrophilic may be achieved. The resin may be contained in a third fluid which is different from both the first fluid and the second fluid.

The surface treatment is not limited to the above-mentioned surface modification of the composite phthalocyanine that is carried out between the processing surfaces 1 and 2, but also may be carried out after the composite phthalocyanine has been discharged from between the processing surfaces 1 and 2. In this case, after the fluid containing the composite phthalocyanine has been discharged from between the processing surfaces 1 and 2, a material to be used for aiming at the surface treatment of the composite phthalocyanine is added into the fluid, and then an operation such as an agitation operation is performed so as to conduct the surface treatment of the composite phthalocyanine. Alternatively, the surface treatment may be executed in such a way that, after the fluid containing the composite phthalocyanine has been discharged, impure materials are removed from the fluid containing the composite phthalocyanine by using a dialysis tube or the like, and then a material to be used for aiming at the surface treatment is added. Further the fluid containing the composite phthalocyanine that has been discharged from the processing surfaces 1 and 2 is made to powder of the composite phthalocyanine by drying the liquid portion of the fluid, and then the surface treatment may be conducted. Specifically, this surface treatment may be executed such that, after the obtained powder of the composite phthalocyanine has been dispersed in an intended solvent, a material to be used for aiming at the surface treatment is added into the dispersion, and then an operation such as an agitation operation is conducted.

As the method for producing the composite phthalocyanine, for example, when the micro reactor with the type of a forced thin film such as the one shown in FIG. 1 is used, the Reynolds number of its minute flow path can be freely changed; and thus, the composite phthalocyanine which is monodisperse and excellent in re-dispersibility, and which has intended properties such as particle size, particle shape, and crystal type, can be formed. In this case, the separation reaction can be completed in the forced thin film formed in the space such as between two discs of the micro reactor. Moreover, by its self-dischargeability, not only there is no clogging with the product even in a reaction accompanied by separation, but also a large pressure is not necessary. Accordingly, the composite phthalocyanine microparticle can be stably produced; and in addition, the production method is superior in safety and excellent in washing performance, and the product thereof is not contaminated with impurities. In addition, not only the method can be scaled up depending on the intended production amount, but also the present invention can provide a highly productive method for producing the composite phthalocyanine.

In addition, the production method of the present invention has the step (3) in which the composite phthalocyanine obtained in the step (2) is subjected to the action of an organic solvent (a third solvent).

In the production method of the present invention for producing a composite phthalocyanine microparticle, the organic solvent is preferably a solvent based on an aromatic compound or a solvent based on a heterocyclic compound. Especially, the solvent based on an aromatic compound or the solvent based on a heterocyclic compound which can induce or facilitate crystal transformation from the alpha-type copper phthalocyanine to the beta-type crystal structure or the like which is usually more stable than the alpha-type copper phthalocyanine may be exemplified.

In the present invention, illustrative example of the organic solvent includes solvents based on aromatic compounds such as styrene, xylene, toluene, benzene, cresol and cumene; solvents based on heterocyclic compounds such as tetrahydrofuran (THF) and pyridine; ketone-based solvents such as methyl ethyl ketone (MEK) and acetone; and polyalcohol-based solvents such as ethylene glycol and propylene glycol. Among them, for example, styrene, xylene, toluene, benzene, cresol, cumene, and THF are preferable. These may be used singly or as a combination of two or more of them.

In the step (3), any publicly known method may be employed in the way how the organic solvent acts on the composite phthalocyanine obtained in the step (2) (sometimes this action is referred to as "organic solvent treatment"). Illustrative example of the method includes a method in which the composite phthalocyanine is introduced into the organic solvent, a method in which the composite phthalocyanine is washed with the organic solvent, a method in which the composite phthalocyanine, while being stirred in water, is introduced into the organic solvent to cause mixing of them, and a method in which the composite phthalocyanine in the state of powder or wet cake containing water or an organic solvent is introduced into the organic solvent with stirring to cause mixing of them. Alternatively, the action of the organic solvent on the composite phthalocyanine may be conducted by an operation such as mere contact or spraying.

In the case that the composite phthalocyanine is soaked in the organic solvent in the step (3), concentration of the composite phthalocyanine may be, for example, in the range of 0.0005 to 95 wt % (both inclusive), or in the range of 1 to 50 wt % (both inclusive), or in the range of 10 to 30 wt % (both inclusive). Meanwhile, in the case that two or more organic solvents are used, the concentration in the organic solvent is relative to total amount of the organic solvents used.

Phthalocyanines of the copper phthalocyanine, the titanyl phthalocyanine, and the cobalt phthalocyanine each undergoes grain (crystal) growth of its own in a certain organic solvent. That is to say, when a certain organic solvent is acted on the individual phthalocyanine, before and after the action the changes can be seen in the crystal growth and crystal type as well as in the spectrum or the like accompanied with the changes in the crystal growth and crystal type. At this time, the crystal type coincides with the spectrum shape.

When the respective phthalocyanines are transformed to the composite phthalocyanine, it may be in a new state in which the growth directions of individual phthalocyanines are suppressed; and thus, in the composite phthalocyanine, each phthalocyanine acts at least on the growth point (the point of growth in the particles or crystals caused by action of a certain organic solvent) of the each phthalocyanine to suppress the growth thereof, resulting in expression of new spectrum characteristics etc. that could never have been expressed. Meanwhile, although the shape of the composite phthalocyanine is not clear, each phthalocyanine is presumably present in the position where it can act at least on the growth point of the each phthalocyanine. The particle in this case is presumably in the state of a solid solution, but the state other than the solid state may be possible.

Meanwhile, similarly to the step (1), the step (3) is preferably conducted also by using the high speed agitator as mentioned before. By so doing, the organic solvent can uniformly act on the phthalocyanine microparticle obtained in the step (2), so that the particle diameter and particle shape or the composition in the composite phthalocyanine microparticle can be made uniform.

On the other hand, in the production method of the present invention, a micro reactor may be used. In the production method of the present invention, it is preferable that at least the step (2) be conducted by using the micro reactor. As for the micro reactor to be used in the present invention, any publicly known micro reactor may be used so far as the present invention can be conducted.

For example, in the method of the present invention for producing a composite phthalocyanine microparticle, at least the step (2) may be executed by using the micro reactor to cause the reaction of at least two fluids to be processed wherein of the fluids to be processed, at least one fluid to be processed is the dissolved solution and the other fluid to be processed is the second solvent.

Especially in the present invention, it is preferable that the micro reactor have the mechanism that in the reaction site of the fluids to be processed, the reaction is facilitated by relative movement of the processing surfaces to each other with keeping a minute distance.

Also, in the method of the present invention for producing a composite phthalocyanine microparticle, at least the step (2) may be executed in the micro reactor wherein at least two fluids to be processed are introduced into between a first processing surface and a second processing surface which are disposed in a position they are faced with each other so as to be able to approach to and separate from each other, at least one of which rotates relative to the other; a separating force which acts in a direction to separate the first processing surface and the second processing surface from each other is generated by an introduction pressure imparted to between the first processing surface and the second processing surface; with keeping a minute distance between the first processing surface and the second processing surface, the at least two fluids to be processed are caused to converge with each other between the first processing surface and the second processing surface that are kept at the minute distance thereby causing to pass the fluids to be processed through between the first processing surface and the second processing surface so as to form a thin film fluid; and the fluids to be processed are made to react with each other in the thin film fluid. In this embodiment, of the fluids to be processed, the at least one fluid to be processed may be the dissolved solution and the other fluid to be processed may be the second solvent.

The micro reactor shown in FIG. 1 is the same as the apparatus that is described in Patent Document 5 and Patent Document 6. The contents of these Documents are incorporated as the content of the present invention so far as it does not deviate from the scope of the present invention; and if necessary they may be arbitrarily combined so as to be used herein. Hereunder, the micro reactor will be described in detail.

The microreactor is provided with two processing members of a first processing member 10 and a second processing member 20 arranged opposite to each other, wherein the first processing member 10 rotates. The surfaces arranged opposite to each other of the respective processing members 10 and 20 are made to be the respective processing surfaces. The first processing member 10 is provided with a first processing surface 1 and the second processing member 20 is provided with a second processing surface 2.

Each of the processing surfaces 1 and 2 is connected to a flow path d1 and d2 of each of the fluids to be processed and constitutes part of the flow path of the fluids to be processed. Distance between these processing surfaces 1 and 2 is controlled so as to form a minute space usually in the range of 1 mm or less, for example, in the range of 0.1 μm to 50 μm. By so doing, the fluids to be processed passing through between the processing surfaces 1 and 2 become a forced thin film fluid forced by the processing surfaces 1 and 2.

By so doing, this apparatus performs a fluid processing in which the first and second fluids to be processed are made to react with each other to separate the microparticle between the processing surfaces 1 and 2.

To more specifically explain, this apparatus is provided with a first holder 11 for holding the first processing member 10, a second holder 21 for holding the second processing member 20, a surface-approaching pressure imparting mechanism 43, a rotation drive mechanism (not shown in drawings), a first introduction part d1, a second introduction part d2, and fluid pressure imparting mechanisms p1 and p2. The fluid pressure imparting mechanisms p1 and p2 can be compressors or other pumps.

In the above-mentioned embodiment, the first processing member 10 and the second processing member 20 are disks with ring forms. Material of the processing members 10 and 20 is not only metal but also carbon, ceramics, sintered metal, abrasion-resistant steel, sapphire, other metals subjected to hardening treatment, and rigid materials subjected to lining, coating, or plating. In the processing members 10 and 20 of the above-mentioned embodiment, the first and second surfaces 1 and 2 arranged opposite to each other are mirror-polished, and the arithmetic average roughness thereof is in the range of 0.01 to 1.0 μm.

In the above-mentioned embodiment, the second holder 21 is fixed to the apparatus, and the first holder 11 attached to a rotary shaft of the rotation drive mechanism fixed to the same apparatus rotates, and thereby the first processing member 10 attached to this first holder 11 rotates relative to the second processing member 20. As a matter of course, the second processing member 20 may be made to rotate, or the both may be made to rotate.

In the present invention, the rotation can be set to a speed of, for example, in the range of 350 to 3600 rpm.

In the above-mentioned embodiment, the second processing member 20 approaches to and separates from the first processing member 10 in the direction of the rotary shaft 50, wherein a side opposite to the second processing surface 2 of the second processing member 20 is accepted in an accepting part 41 arranged in the second holder 21 so as to be able to rise and set. However, in contrast to the above, the first processing member 10 may approach to and separate from the second processing member 20, or both the processing members 10 and 20 may approach to and separate from each other.

The above-mentioned accepting part 41 is a concave portion for accepting the side opposite to the second processing surface 2 of the second processing member 20, and this concave portion is a groove being formed into a ring. This accepting part 41 accepts the second processing member 20 with sufficient clearance so that the side opposite to the second processing surface 2 of the second processing member 20 may rise and set.

The surface-approaching pressure imparting mechanism is a mechanism to generate a force (hereinafter, surface-approaching pressure) to press the first processing surface 1 of the first processing member 10 and the second processing surface 2 of the second processing member 20 in the direction to make them approach to each other. The mechanism generates a thin film fluid having a minute thickness in a level of nanometer or micrometer while keeping the distance between the processing surfaces 1 and 2 in a predetermined minute distance by the balance between the surface-approaching pressure and the force due to the fluid pressure to separate the processing surfaces 1 and 2 from each other. In the above-mentioned embodiment, the surface-approaching pressure imparting mechanism supplies the surface-approaching pressure by biasing the second processing member 20 toward the first processing member 10 by a spring 43 arranged in the second holder 21.

In addition, the first fluid to be processed which is pressurized with the fluid pressure imparting mechanism p1 is introduced from the first introduction part d1 to the space inside the processing members 10 and 20.

On the other hand, the second fluid to be processed which is pressurized with the fluid pressure imparting mechanism p2 is introduced from the second introduction part d2 via a path arranged inside the second processing member 20 to the space inside the processing members 10 and 20 through an opening d20 formed in the second processing surface.

At the opening d20, the first fluid to be processed and the second fluid to be processed converge and mix with each other, thereby effecting oxidation, reduction, separation, or crystallization.

At this time, the mixed fluid to be processed becomes a forced thin film fluid by the processing surfaces 1 and 2 that keep the minute space therebetween, whereby the fluid is forced to move out from the circular, processing surfaces 1 and 2. The first processing member 10 is rotating; and thus, the mixed fluid to be processed does not move linearly from inside the circular, processing surfaces 1 and 2 to outside thereof, but does move spirally from the inside to the outside thereof by a resultant vector acting on the fluid to be processed, the vector being composed of a moving vector toward the radius direction of the circle and a moving vector toward the circumferential direction.

Figure 2:
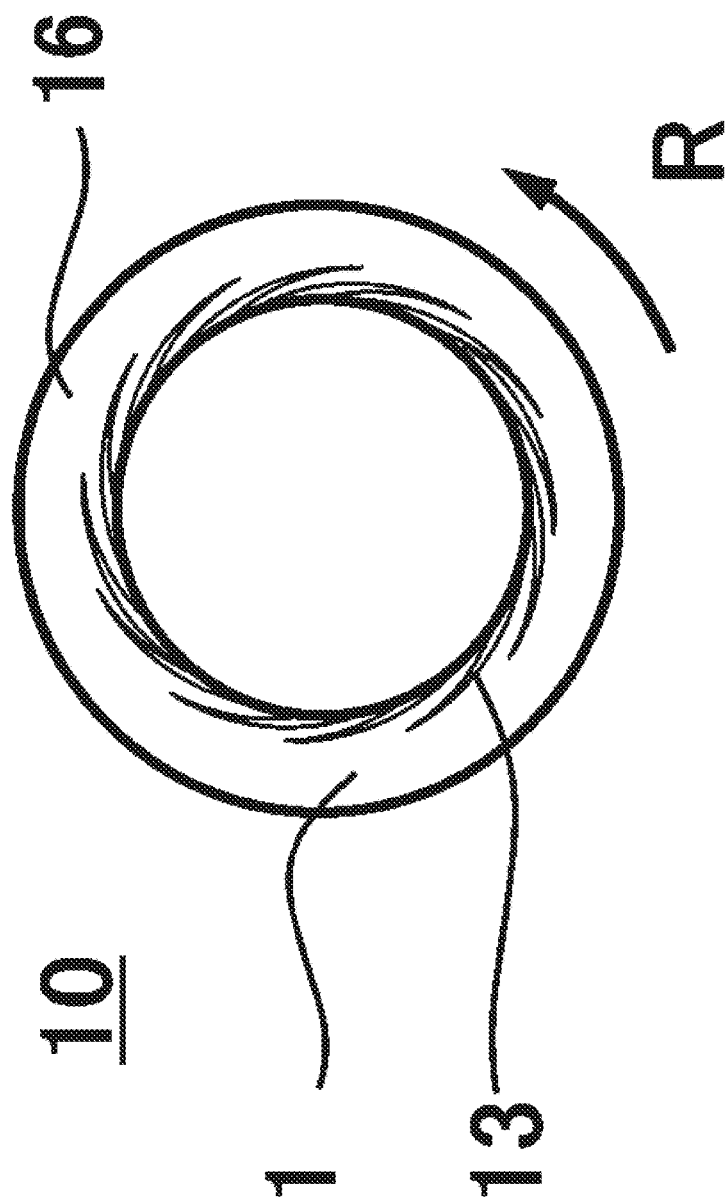

Here, as shown in FIG. 2, in the first processing surface 1 of the first processing member 10, a groove-like depression 13 extended toward an outer side from the central part of the first processing member 10, namely in a radius direction, may be formed. The depression 13 may be, as a plane view, curved or spirally extended on the first processing surface 1, or, though not shown in the drawing, may be extended straight radially, or bent at a right angle, or jogged; and the concave portion may be continuous, intermittent, or branched. In addition, this depression 13 may be formed also on the second processing surface 2, or on both the first and second processing surfaces 1 and 2. By forming the depression 13 as mentioned above, the micro-pump effect can be obtained so that the fluid to be processed may be sucked into between the first and second processing surfaces 1 and 2.

It is preferable that the base edge of the depression 13 reach the inner periphery of the first processing member 10. The front edge of the depression 13 is extended to the direction of the outer periphery of the first processing surface 1; the depth thereof is made gradually shallower (smaller) from the base edge to the front edge. Between the front edge of the depression 13 and the outer peripheral of the first processing surface 1 is formed a flat plane not having the depression 13.

The opening d20 described above is arranged preferably at a position opposite to the flat surface of the first processing surface 1. By so doing, mixing of a plurality of fluids to be processed and separation of the microparticle therefrom can be effected under the condition of a laminar flow.

In addition, the fluid discharged to outside the processing members 10 and 20 is collected via a vessel v into a beaker b as a discharged solution. In the embodiment of the present invention, the discharged solution contains the composite phthalocyanine microparticle to be described later. Meanwhile, the beaker b is not particularly restricted to a beaker; it may be a tank or a drum, or alternatively, direct connection to the subsequent step such as a step to use filtration equipment may be allowed.

Although, in the embodiment shown in FIG. 1, kinds of the fluid to be processed and numbers of the flow path thereof are set two respectively, they may be three or more. The opening for introduction arranged in each processing member is not particularly restricted in its form, size, and number; and these may be changed as appropriate. The opening for introduction may be arranged just before the first and second processing surfaces 1 and 2 or in the side of further upstream thereof.

In the present invention, it is good enough only if the treatment could be effected between the processing surfaces 1 and 2; and an embodiment that the second fluid to be processed is introduced from the first introduction part d1 and the first fluid to be processed is introduced from the second introduction part d2 may also be used. For example, the expression "first" or "second" for each fluid has a meaning for merely discriminating an $n^{th}$ fluid among a plurality of the fluids present; and therefore, a third or more fluids can also exist as described before.

In the production method of the present invention, it is preferable to conduct at least the step (2) by using the micro reactor; however, the step (2) and the step (3) may be continuously conducted by using the micro reactor. Specifically, as shown in FIG. 1 (B), besides the first introduction part d1 and the second introduction part d2, the third introduction part d3 is arranged in the micro reactor; and for example, the dissolved solution is introduced as the first fluid from the first introduction part d1, the second solvent is introduced as the second fluid from the second introduction part d2, and the organic solvent is introduced as the third fluid from the third introduction part d3; the respective fluids being separately introduced into the micro reactor. In this case, the third introduction part d3 through which the organic solvent is introduced is arranged in the downstream side of the first introduction part d1 and the second introduction part d2; and to be more specific, by arranging the opening d30 of the third introduction part d3 in the downstream side of the opening d20 of the second introduction part d2, the organic solvent can act on the composite phthalocyanine microparticle separated between the processing surfaces 1 and 2. The micro reactor provided with the three openings (d10, d20, and d30) is suitable when the step (2) and the step (3) are continuously conducted.

However, in execution of the present invention, in the case that the step (2) is conducted in the micro reactor and the steps after the step (2) are conducted outside the micro reactor, at least two openings (d10 and d20) are enough, as shown in FIG. 1 (A). However, in the case that the surface treatment is conducted in the thin film fluid onto the composite phthalocyanine microparticle separated between the processing surfaces 1 and 2, though not limited to this case, it does not preclude to conduct the step (2) by using the micro reactor provided with three or more openings.

In addition, in the present invention, as the case may be, the composite phthalocyanine microparticle obtained in the step (2) may be washed and/or subjected to solvent substitution. Washing and/or solvent substitution may be arbitrarily conducted by using publicly known methods. Though not particularly restricted, with regard to the solution containing the composite phthalocyanine microparticle, washing and/or solvent substitution of the composite phthalocyanine may be conducted by way of operation such as filtration, centrifugation, and ultrafiltration, wherein the solvent is selected in accordance with the object.

In the present invention, the term "microparticle" means fine crystal or aggregate of crystals having the size of submicron order (nano-order). Shape of the microparticle is not particularly restricted, whereby it may be particle or aggregate of particles having the shape of, for example, a quasi-cylindrical column, a quasi-sphere, a quasi-disk, a quasi-triangular prism, a quasi-square pillar, a quasi-polygonal, an elliptical sphere, etc.

The composite phthalocyanine microparticle of the present invention is the composite phthalocyanine microparticle including at least the copper phthalocyanine and the titanyl phthalocyanine and/or the cobalt phthalocyanine, wherein the aspect ratio thereof is in the range of 1.1 to 2.5 (both inclusive) and the particle diameter is in the range of 5 to 100 nm (both inclusive). For example, by using the production method of the present invention, the composite phthalocyanine microparticle with the size thereof being in a level of nanometers, preferably in a 100 nm order, optimal as the coloring material, can be obtained.

The aspect ratio may also be in the range of 1.0 to 5.0 (both inclusive), or in the range of 1.1 to 2.5 (both inclusive), or in the range of 1.5 to 2.0 (both inclusive). Also the particle diameter may be in the range of 2 to 80 nm, or in the range of 5 to 50 nm, or in the range of 10 to 30 nm. On the other hand, in conventional methods, for example, because of the crystal transformation to the beta-type crystal structure or the like, which is usually more stable than the alpha-type, the aspect ratio and particle diameter become larger, so that not only to produce the microparticle having the small aspect ratio and particle diameter like those of the present invention has been difficult, but also there have been no production examples of the microparticle like this.

In the composite phthalocyanine microparticle of the present invention, the relative value of Abs (a) at the peak top in the range of 655 to 700 nm of the UV-visible absorption spectrum thereof to Abs (b) at the peak top in the range of 550 to 640 nm of the same ([Abs(a)]/[Abs(b)]) is preferably 0.8 or more. For example, by using the production method of the present invention, the composite phthalocyanine microparticle provided with optimal characteristics as the coloring material with suppressed light scattering, especially having a clearer blue color than ever, can be obtained.

The Abs (a) at the peak top may also be, for example, "Abs" at the peak top in the range of 660 to 700 nm of the UV-visible absorption spectrum, or "Abs" at the peak top in the range of 660 to 690 nm of the UV-visible absorption spectrum, or "Abs" at the peak top in the range of 650 to 690 nm of the UV-visible absorption spectrum. The Abs (b) at the peak top may also be, for example, "Abs" at the peak top in the range of 560 to 640 nm of the UV-visible absorption spectrum, or "Abs" at the peak top in the range of 550 to 650 nm of the UV-visible absorption spectrum, or "Abs" at the peak top in the range of 540 to 630 nm of the UV-visible absorption spectrum.

The relative value of Abs (a) to Abs (b) ([Abs(a)]/[Abs (b)]) is preferably 0.8 or more; however, the relative value may be in the range of 1.0 to 4.0, or in the range of 1.2 to 3.5, or in the range of 1.4 to 3.0, or in the range of 1.6 to 2.5. When the relative value ([Abs(a)]/[Abs(b)]) is made 1.0 or more, a reddish color of the composite phthalocyanine microparticle becomes less, and a clearer blue color can be developed.

In the present invention, the crystal type of the composite phthalocyanine is defined as the crystal type that is identified by measurement of the dried powder thereof by way of an X-ray diffraction method (XRD).

The composite phthalocyanine microparticle of the present invention is of a blue color or of a bluish color; especially this microparticle can develop a clearer blue color than a conventional copper-titanyl phthalocyanine crystal etc. Because the composite phthalocyanine microparticle of the present invention is capable of being especially a coloring material having a clearer blue color and the like, this can be utilized in various uses such as an ink, an ink for jet, an ink for thermal transfer, a toner, a paint (architecture, automobile, etc.), a colored resin, and a color filter.

EXAMPLES

Hereinafter, examples and so forth specifically illustrating the composition and effect of the present invention will be described. Meanwhile, the present invention is not limited to the following examples.

In Examples, in the case that the micro reactor with the type of a forced thin film is used, "A solution" is defined as the first fluid to be processed that is introduced from the first introduction part d1 of the apparatus shown in FIG. 1 (A); and "B solution" is defined as the second fluid to be processed that is introduced from the second introduction part d2 of the same apparatus. Meanwhile, the operation condition of the micro reactor with regard to the rotation number of the discs is 1700 rpm. In Examples, $H_2SO_4$ stands for concentrated sulfuric acid, CuPc stands for the copper phthalocyanine, TiOPc stands for the titanyl phthalocyanine, and CoPc stands for the cobalt phthalocyanine. In addition, for example, CuPc_TiOPc stands for the copper-titanyl phthalocyanine.

Example 1

(Step 1 and Step 2)
By using ULREA SS-11 (manufactured by M. Technique Co., Ltd.) as the micro reactor with the type of a forced thin film, the copper-titanyl phthalocyanine microparticles were produced with the production condition 1 described below. Firstly, the copper phthalocyanine and the titanyl phthalocyanine, the raw materials of this Example, were mixed with and dissolved into concentrated sulfuric acid to prepare a dissolved solution (step 1); and the dissolved solution thus obtained and a solvent (pure water) capable of being a good solvent to the raw materials were mixed by using ULREA SS-11 to separate the composite phthalocyanine microparticles. The discharged solution containing the composite phthalocyanine microparticles was discharged from between the processing surfaces 1 and 2 (step 2).
(Production Condition 1)
A solution: pure water
B solution: 2.1 wt % CuPc/0.9 wt % TiOPc/97 wt % (98 wt % concentrated sulfuric acid); CuPc/TiPPc=70/30=2.33 (weight ratio)
Preparation of B solution: Clearmix (CLM-2.2S, manufactured by M. Technique Co., Ltd.)
    Rotation number: 20000 rpm
    Preparation time: 30 minutes
    Preparation temperature: 30° C. (Preparation amount: 470 g=300 cc)
ULREA SS-11
    A/B flow rate: 400/30 mL/min
    A/B supply temperature: 25/25° C.
    Disc rotation number: 1700 rpm
(Washing and Solvent Substitution)
Next, as the subsequent step, the discharged solution was filtrated to recover the composite phthalocyanine microparticles. The obtained wet cake of the composite phthalocyanine microparticles was introduced into pure water, and it was washed by treating with Clearmix at the rotation number of 5000 rpm for the period of 10 minutes. The obtained slurry of the composite phthalocyanine microparticles was filtrated again, and the composite phthalocyanine microparticles were washed. This washing operation was repeated for three times. Then, the obtained wet cake of the composite phthalocyanine microparticles with water was introduced into ethanol; and the obtained composite phthalocyanine microparticles were dispersed into ethanol by treating with Clearmix at the rotation number of 5000 rpm for the period of 10 minutes. The obtained slurry of the composite phthalocyanine microparticles in ethanol as the dispersing medium was filtrated again; by so doing, the solvent substitution of the composite phthalocyanine microparticles was conducted. This solvent substitution operation was repeated for three times.
(Step 3)
Next, the obtained wet cake of the composite phthalocyanine microparticles with ethanol was treated by using styrene to carry out the same treatment as the above-mentioned solvent substitution (styrene treatment), whereby styrene was made to act on the composite phthalocyanine microparticles to obtain the final wet cake thereof with styrene. From the obtained wet cake with styrene, dried powder was produced. In Examples 2 to 4, too, the same solvent substitution and the styrene treatment (each organic solvent treatment) as those of Example 1 were conducted. Part of the wet cake with styrene was diluted with styrene and subjected to the dispersion treatment with styrene to produce the disperse solution thereof. The particle diameter of the composite phthalocyanine microparticles obtained in Example 1 was 24.6 nm, and the aspect ratio of the same was 1.31.

Meanwhile, the particle diameter was obtained from the average value obtained from the measurement results of particle diameters of 100 particles observed with a transmission electron microscopy (TEM). The aspect ratio was obtained from the average value of as the measurement results of the long diameters and the short diameters of 100 particles observed with a transmission electron microscopy (TEM). The TEM observation was made by using the transmission electron microscope JEM-2100 (manufactured by JEOL Ltd.). The observation conditions were the acceleration voltage of 80 kV and the observation magnification of 10000 and 50000. The above-mentioned disperse solution was dropped onto a collodion film, which was followed by drying at room temperature to obtain the sample for TEM observation; by using this sample, the TEM observation was carried out.

Figure 3:
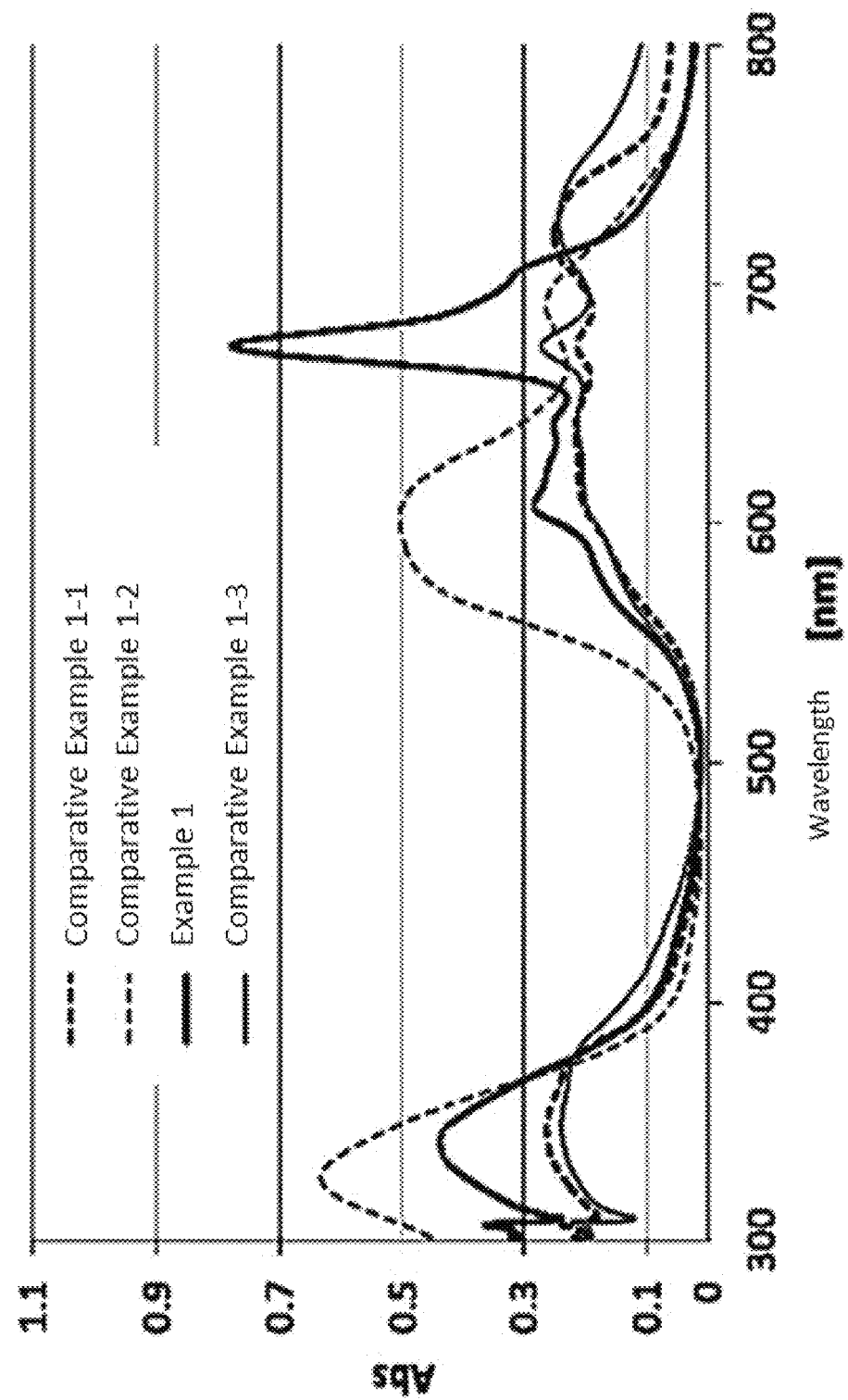
Figure 5:
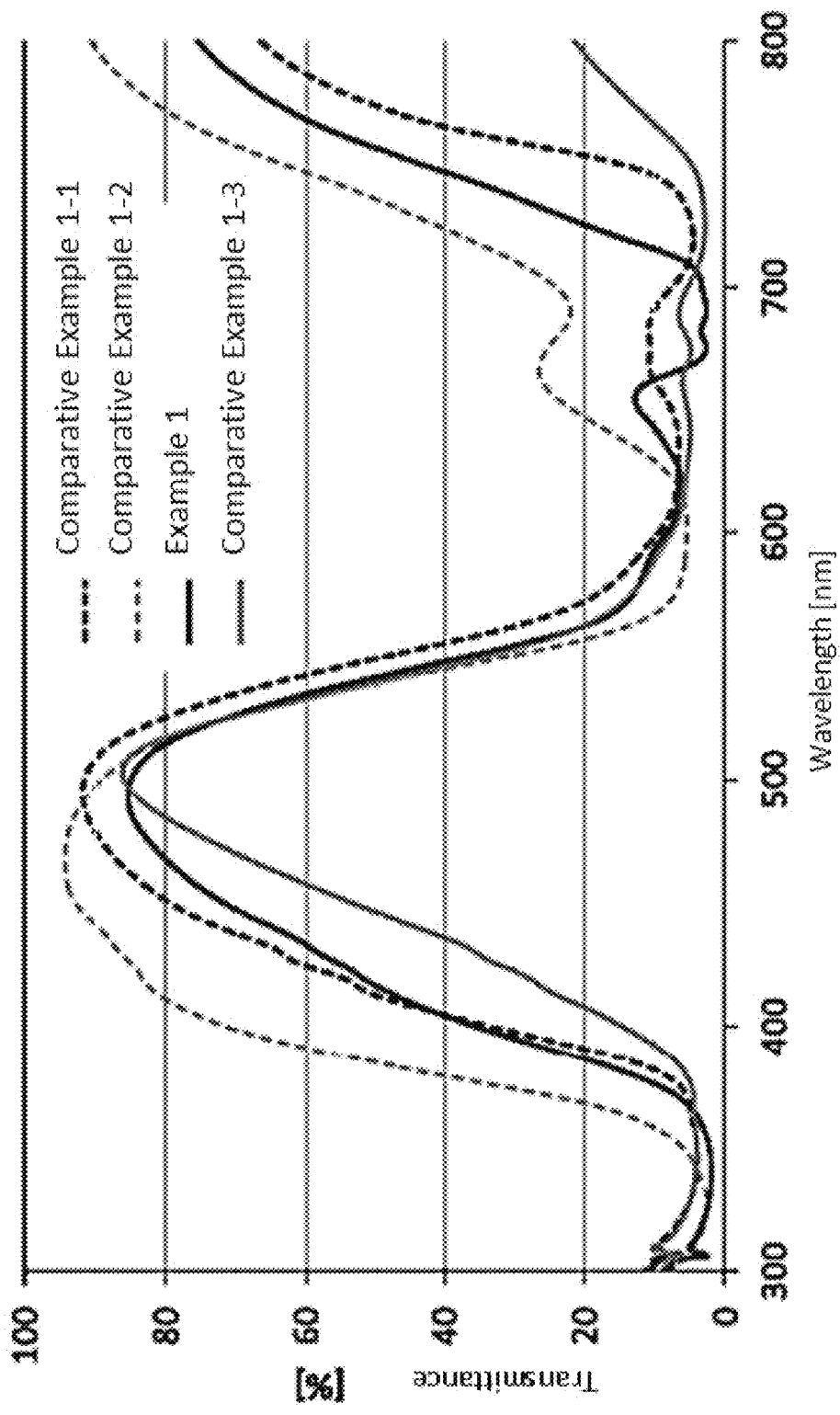

The measurement results of the absorption spectra of Example 1 and the below-described three Comparative Examples against Example 1 are shown in FIG. 3, and the measurement results of the transmission spectra of the same are shown in FIG. 5. The absorption and transmission spectra were measured by using the before-mentioned disperse solution as the measurement sample of the absorption and transmission spectra. Meanwhile, the absorption and transmission spectra were measured in the wavelength range of 300 to 800 nm by using a UV-visible spectrophotometer (UV-2540, manufactured by Shimadzu Corp.).

Meanwhile, Comparative Example 1-1 relates to the copper phthalocyanine whose crystal type is the beta-type, which is the raw material of CuPc used in the B solution of Example 1. Comparative Example 1-2 relates to the cupper-titanyl phthalocyanine microparticles before action of styrene in the step 3 of Example 1. Comparative Example 1-3 relates to the phthalocyanine microparticles produced by using titanyl sulfate in place of the titanyl phthalocyanine of Example 1.

The particle diameters of the microparticles of Comparative Example 1-1 to 1-3 were 116.4 nm, 14.8 nm, and 976.9 nm, respectively; and the aspect ratios of the same were 4.52, 1.03, and 5.99, respectively. Further, the ratio of the particle diameter after the styrene treatment (particle diameter of Example 1) relative to the particle diameter before the styrene treatment (particle diameter of Comparative Example 1-2) was 1.66, indicating that the growth of the particle (crystal) could be suppressed by the styrene treatment.

From FIG. 3, in the copper-titanyl phthalocyanine microparticles obtained in Example 1, the relative value of Abs (a) to Abs (b) ([Abs(a)]/[Abs(b)]) was 2.74, wherein Abs (a) is the absorbance value at the peak top near 673 nm and Abs (b) is the absorbance value at the peak top near 605 nm. This indicates that the copper-titanyl phthalocyanine microparticles obtained in Example 1 are excellent in absorbing capability of a red color in the wavelength range of about 660 to 700 nm.

However, in Comparative Example 1-2, or Comparative Example 1-3 in which $TiOSO_4$ was used, the spectrum shape similar to the Example 1 could not be obtained; especially in Comparative Example 1-3, the microparticles became coarse, only giving the absorption spectrum shape of the crystal type that resembles the CuPc (Comparative Example 1-1) having the beta-type crystal.

From FIG. 5, it can be seen that the copper-titanyl phthalocyanine microparticles obtained in Example 1 have the peak top of the transmitting region of about 400 to 550 nm shifted to the side of a longer wavelength as compared with Comparative Example 1-2 thereby having a purple component eliminated from the conventional copper-titanyl phthalocyanine microparticles (Comparative Example 1-2), and in addition, from FIG. 3, it can be seen that the copper-titanyl phthalocyanine microparticles obtained in Example 1 show the absorption in the wavelength region of 600 to 720 nm thereby having a reddish component eliminated from the conventional copper-titanyl phthalocyanine microparticles. Therefore, the copper-titanyl phthalocyanine microparticles obtained in Example 1 can develop a clearer blue color as compared with the conventional copper-titanyl phthalocyanine microparticles.

On the other hand, as shown in FIG. 3, Comparative Example 1-3, in which $TiOSO_4$ is used, shows the absorption in the wavelength region of 600 to 720 nm; however, as shown in FIG. 5, the peak top of the transmission region of about 400 to 550 nm is excessively shifted to the side of a longer wavelength as compared with Comparative Example 1-2, and because of this, it is presumed that an excessively greenish color is resulted.

Figure 7:
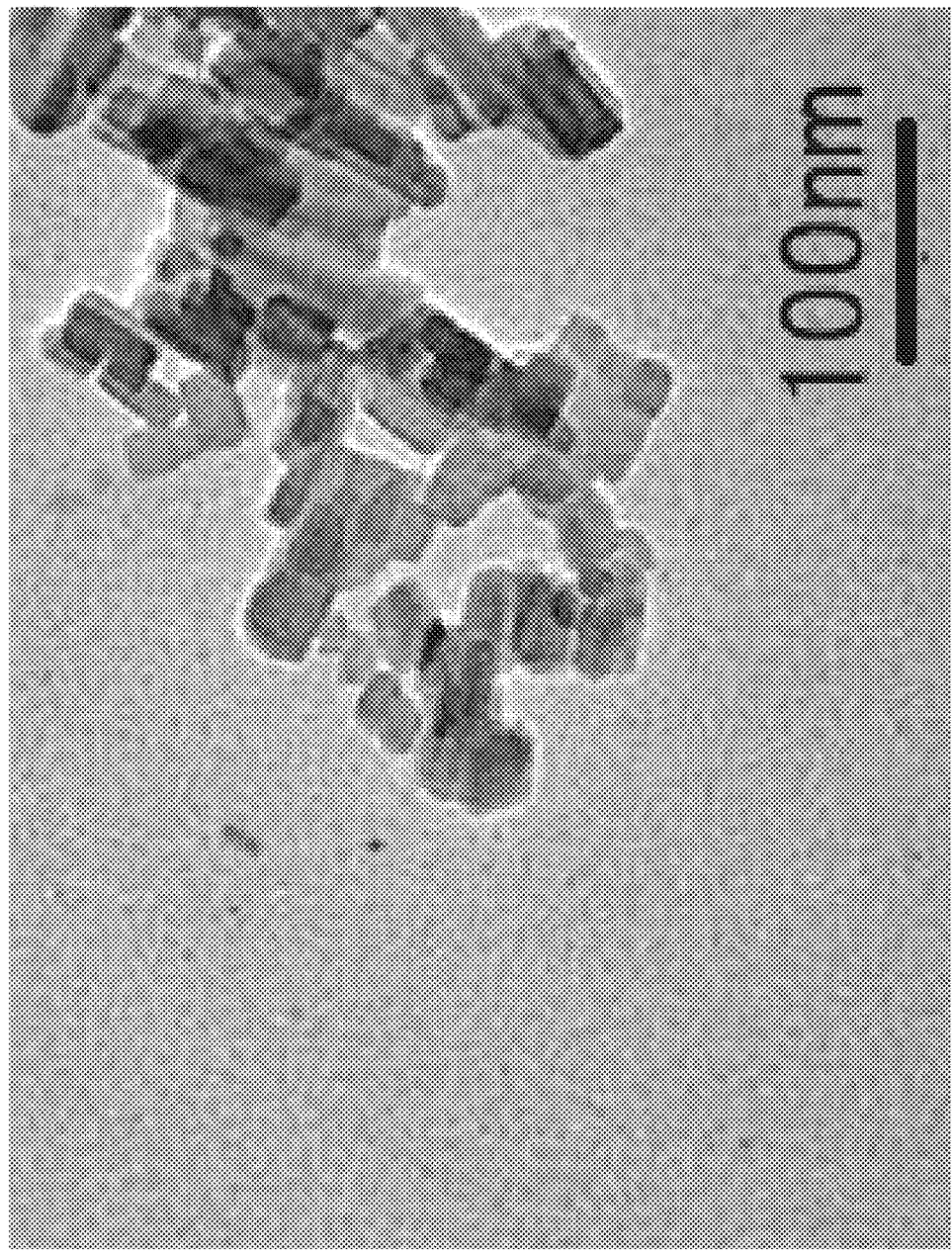
Figure 8:
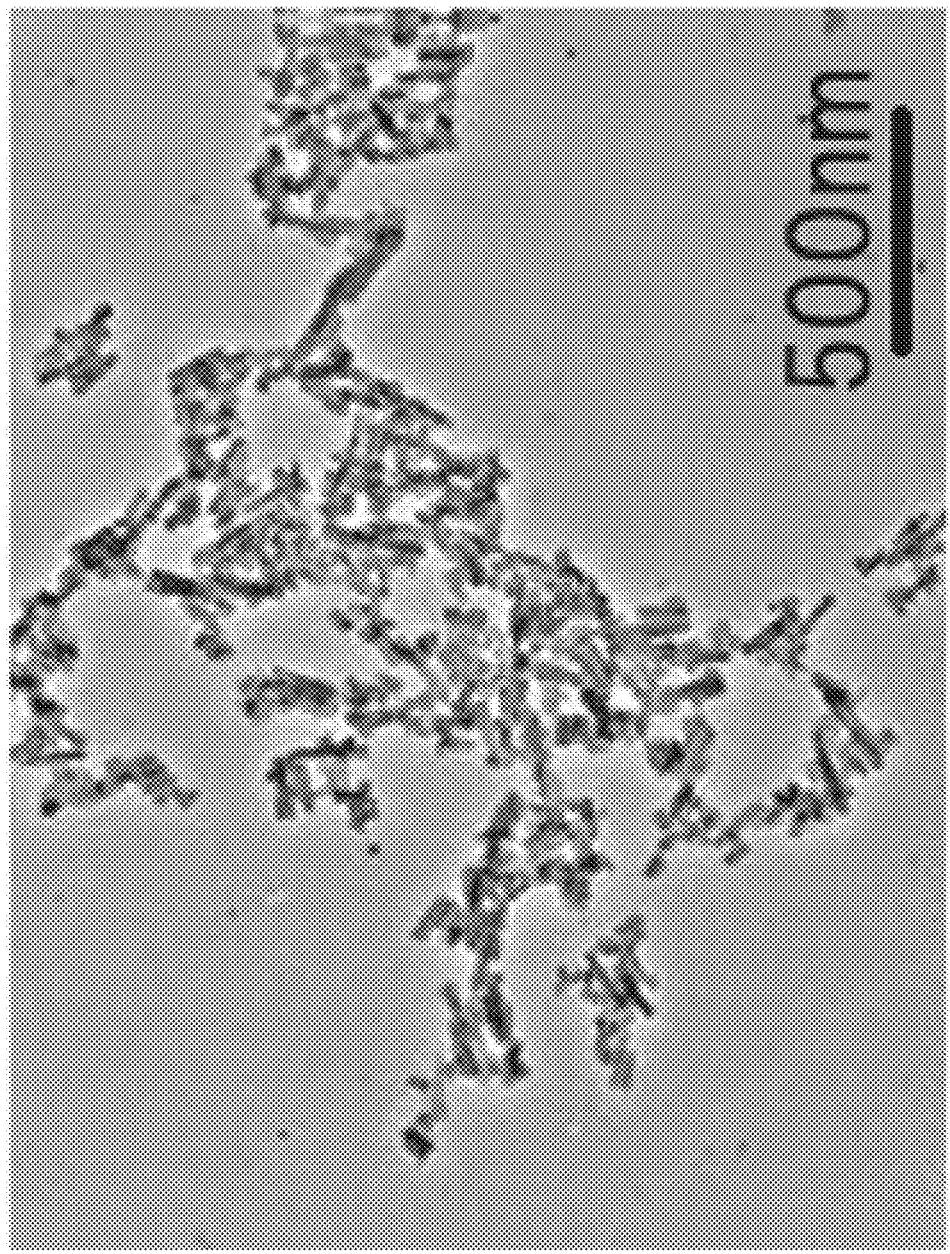
Figure 9:
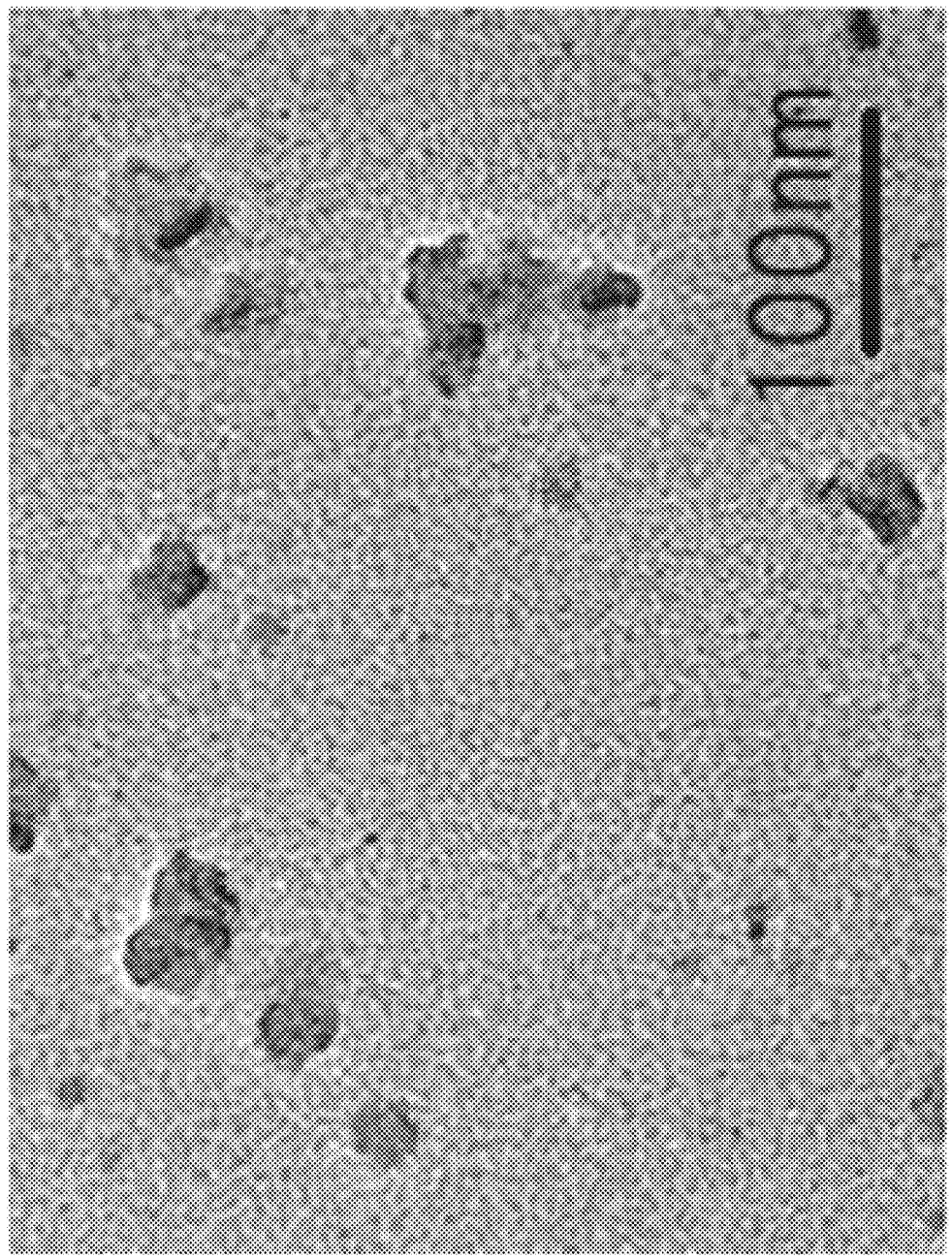
Figure 10:
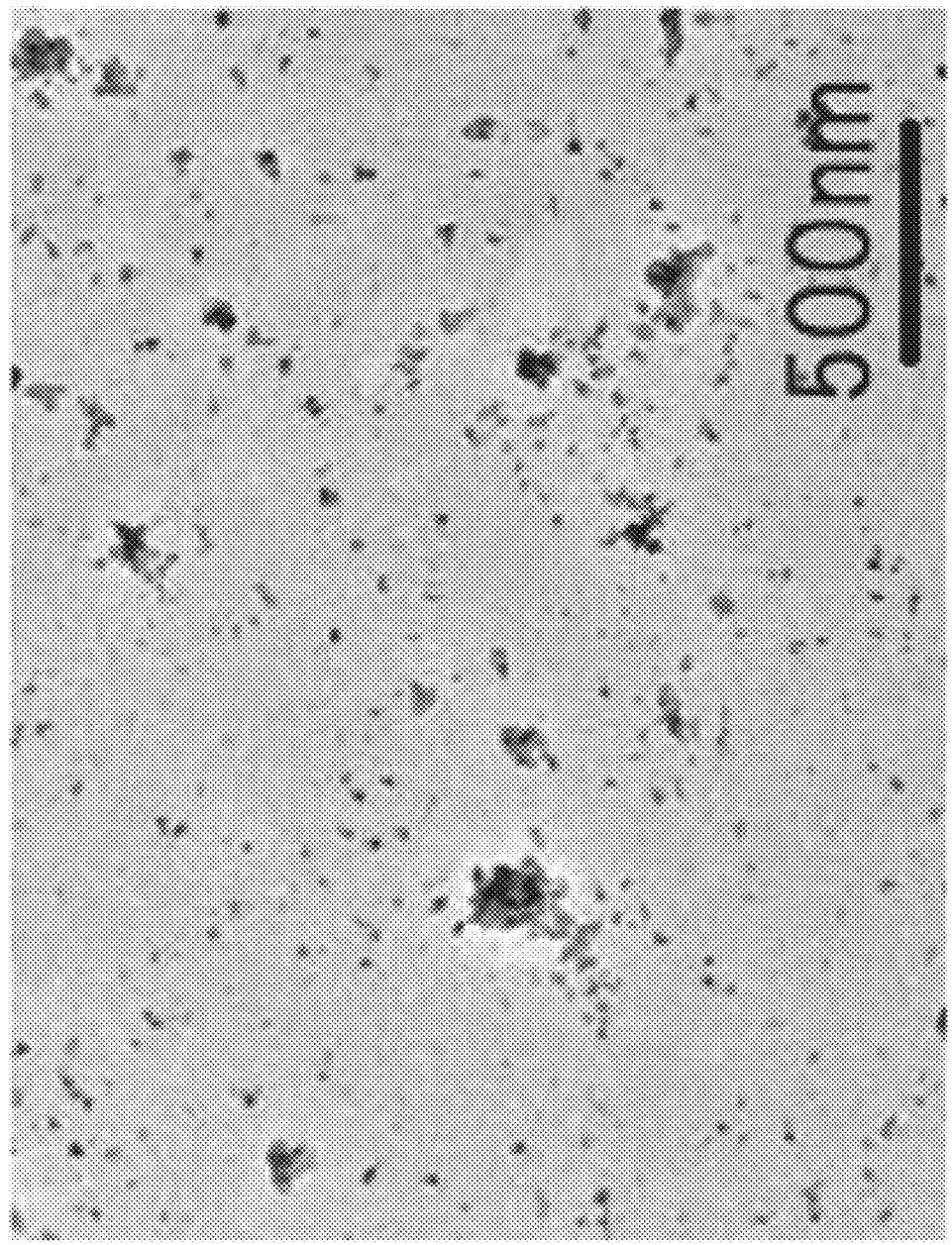

By using the dried powder obtained in Example 1, observation with the transmission electron (TEM) was conducted. In FIG. 7 and FIG. 8, pictures are shown that were obtained by the observation with the transmission electron (TEM) with the magnification of 50000 and 10000, respectively, in Example 1. Also in FIG. 9 and FIG. 10, pictures of the copper-titanyl phthalocyanine microparticles before the action of styrene in the step 3 of Example 1 (Comparative Example 1-2) are shown; the pictures being obtained by the observation with the transmission electron (TEM) with the magnification of 50000 and 10000, respectively.

By using the dried powder obtained in Example 1, the X-ray diffraction measurement (XRD) was conducted. The result thereof is shown in the lower figure of FIG. 13. In the upper figure of FIG. 13, the XRD measurement result of the beta-type CuPc (Comparative Example 1-1), which is the raw material of CuPc used in the B solution of this Example, is shown. In the middle figure of FIG. 13, the XRD measurement result of the copper-titanyl phthalocyanine microparticles before the action of styrene in the step 3 of Example 1 (Comparative Example 1-2) is shown.

Meanwhile, for the XRD measurement, the powder X-ray diffraction measurement apparatus (product name: X'Pert PRO MPD, manufactured by PANalytical B. V.) was used. The measurement conditions were as follows: measurement range of 6 to 60°, Cu anticathode, tube voltage of 45 kV, tube current of 40 mA, and scanning speed of 16°/min.

Figure 13:
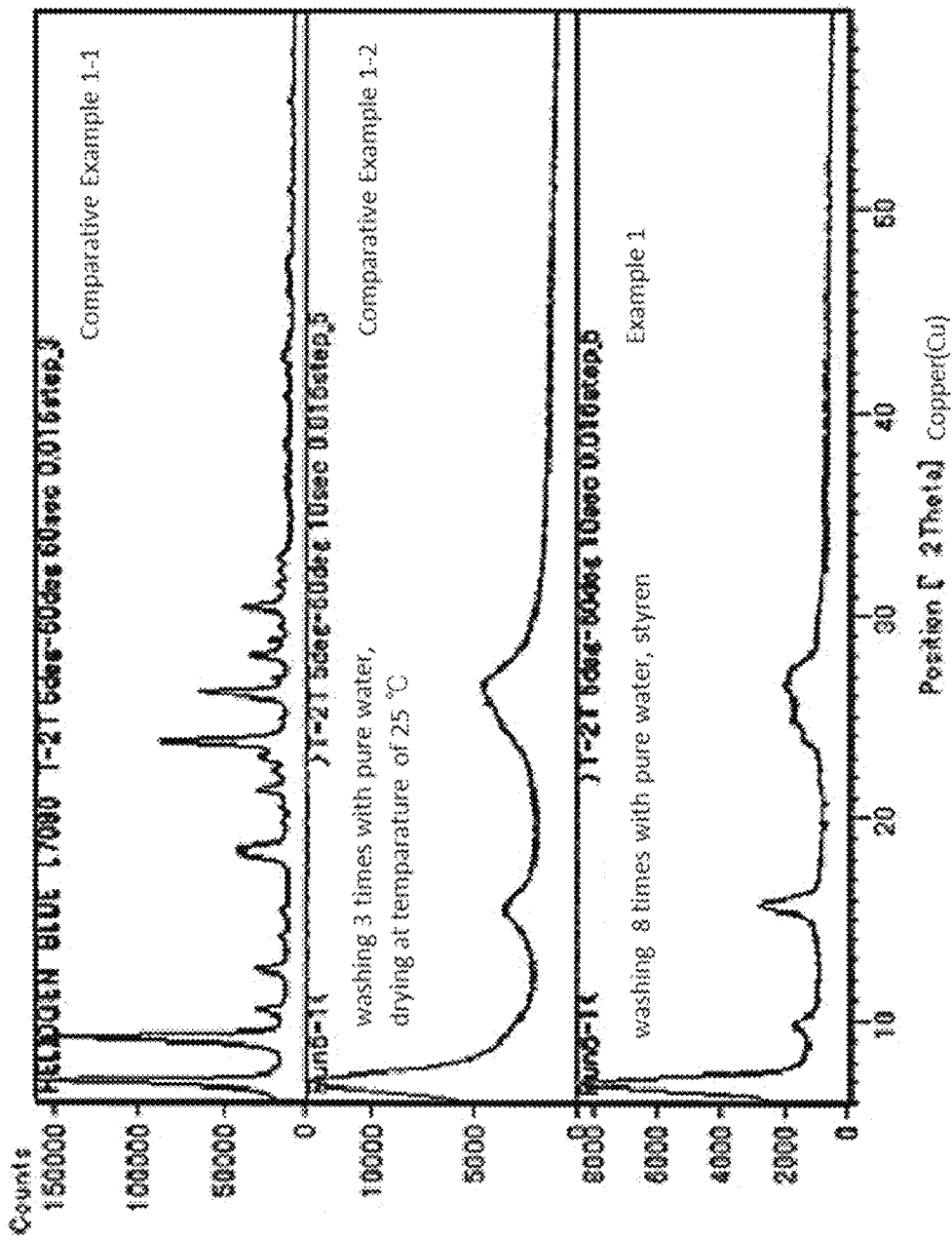

From the results of FIG. 13, even though styrene, which can usually transform the crystal type of the alpha-type CuPc to the beta-type CuPc, is made to act thereto, it can be confirmed that there is no substantial change in the crystal type itself in the copper-titanyl phthalocyanine microparticles of Example 1 as compared with Comparative Example 1-2.

Example 2

The copper-titanyl phthalocyanine microparticles were produced by the production condition 1 which is the same as that of Example 1, except that Cu/Ti=70/30=2.33 (weight ratio) in Example 1 was changed to Cu/Ti=85/15=5.67 (weight ratio). The particle diameter of the copper-titanyl phthalocyanine microparticles obtained in Example 2 was 43.1 nm and the aspect ratio of the same was 1.84.

Figure 4:
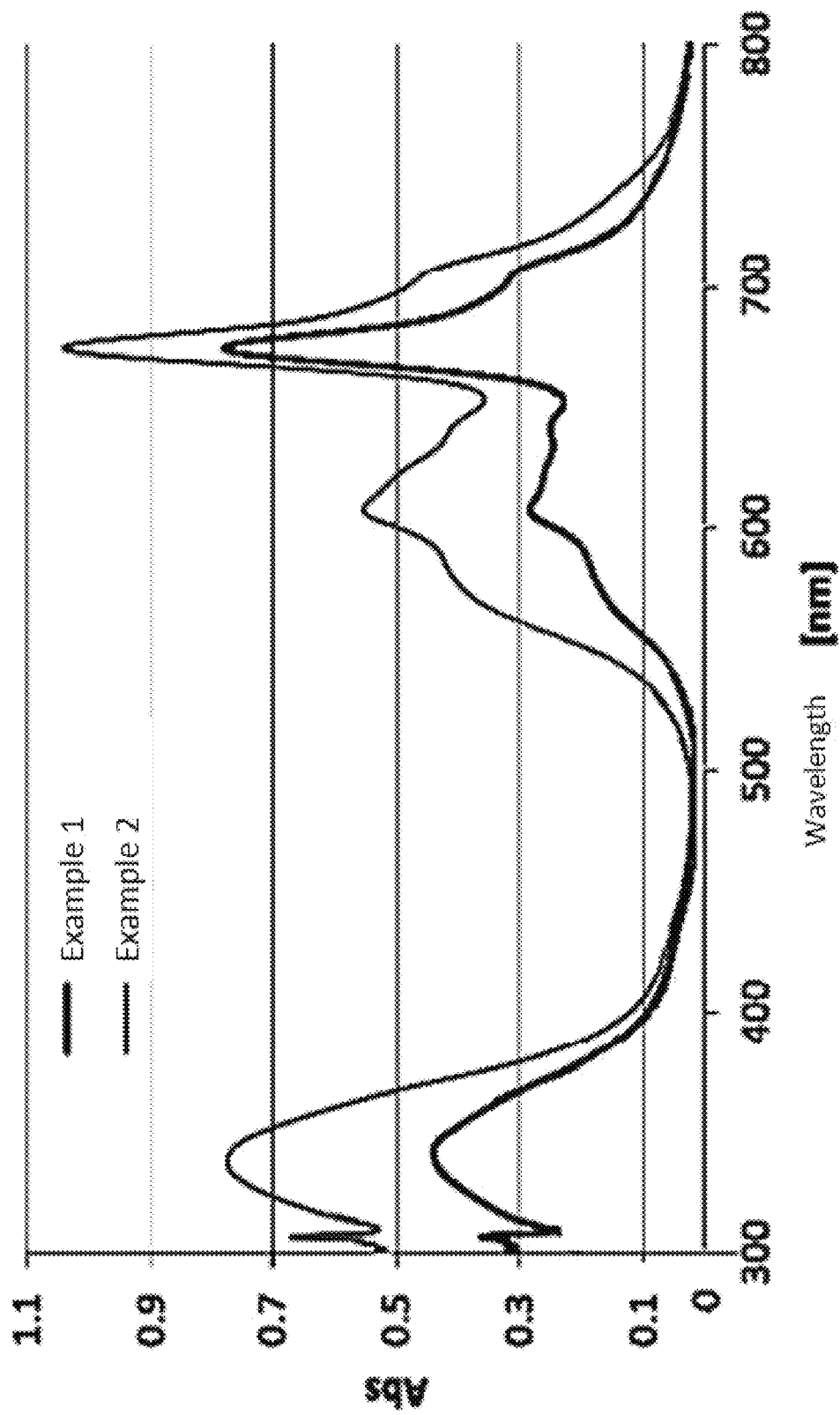
Figure 6:
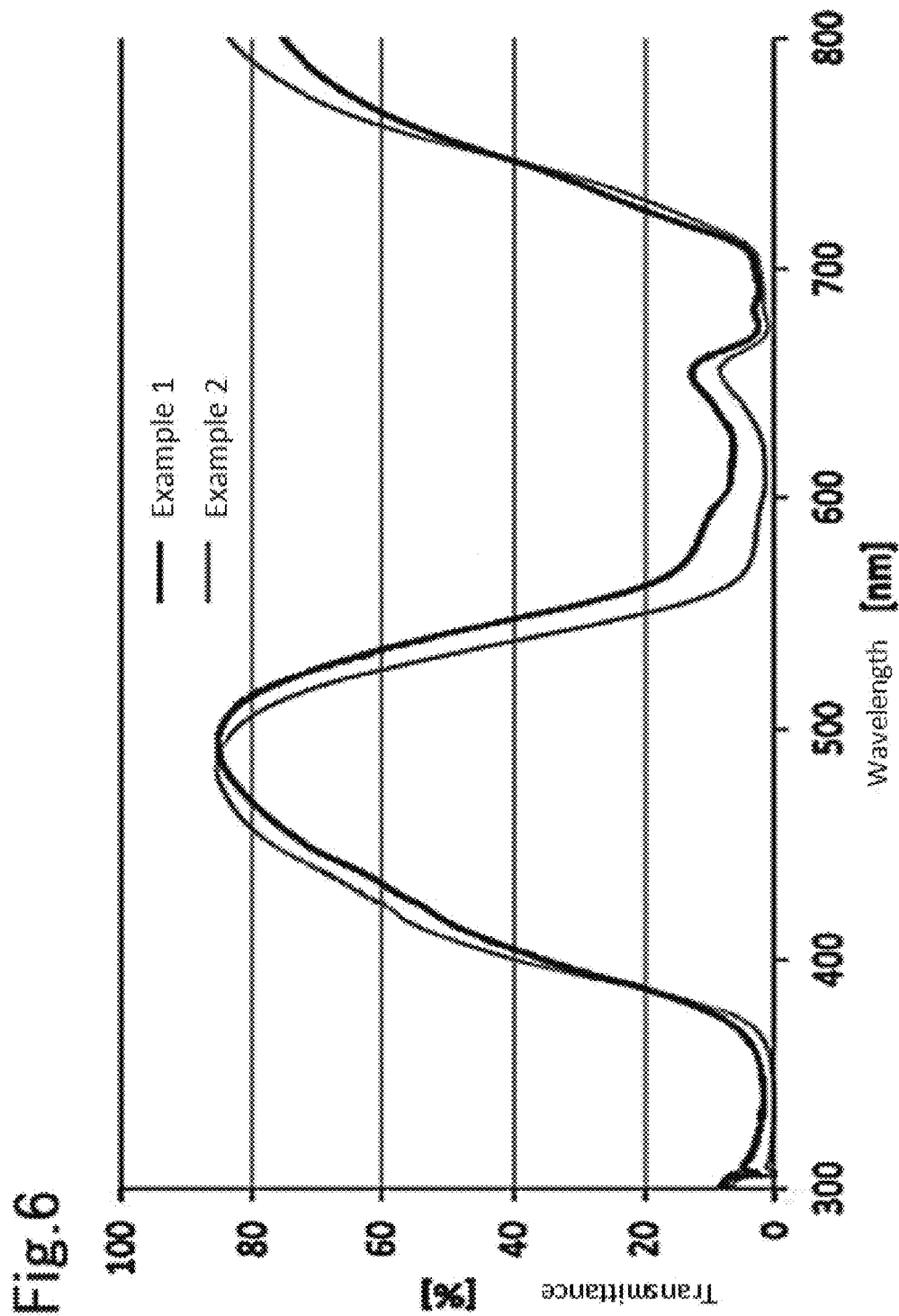

The measurement results of the absorption spectra of Example 1 and Example 2 are shown in FIG. 4, and the measurement results of the transmission spectra of the same are shown in FIG. 6.

From FIG. 4, in the copper-titanyl phthalocyanine microparticles obtained in Example 2, the relative value of Abs (a) to Abs (b) ([Abs(a)]/[Abs(b)]) was 1.89, wherein Abs (a) is the absorbance value at the peak top near 673 nm and Abs (b) is the absorbance value at the peak top near 605 nm.

Comparative Example 2

As Comparative Example 2, the pigment microparticles were produced in the same way as Example 2 except that the titanyl phthalocyanine in Example 2 was changed to the phthalocyanine not having a metal (hereunder, this is described as $H_2Pc$); and the absorption spectrum, the transmission spectrum, and the particle diameter of the same were measured. The particle diameter of the microparticles obtained in Comparative Example 2 was 634.9 nm and the aspect ratio of the same was 5.12.

Figure 19:
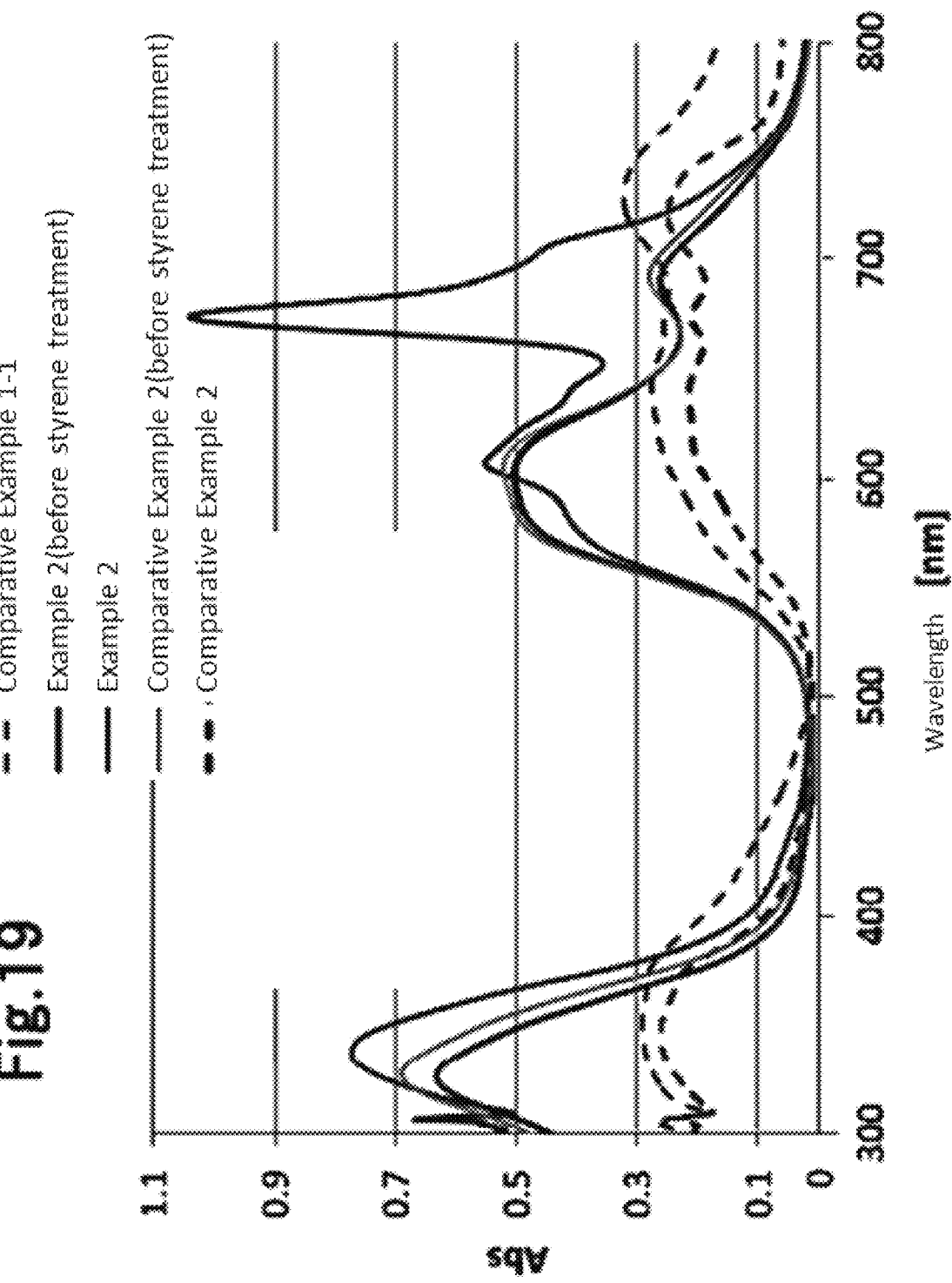
Figure 20:
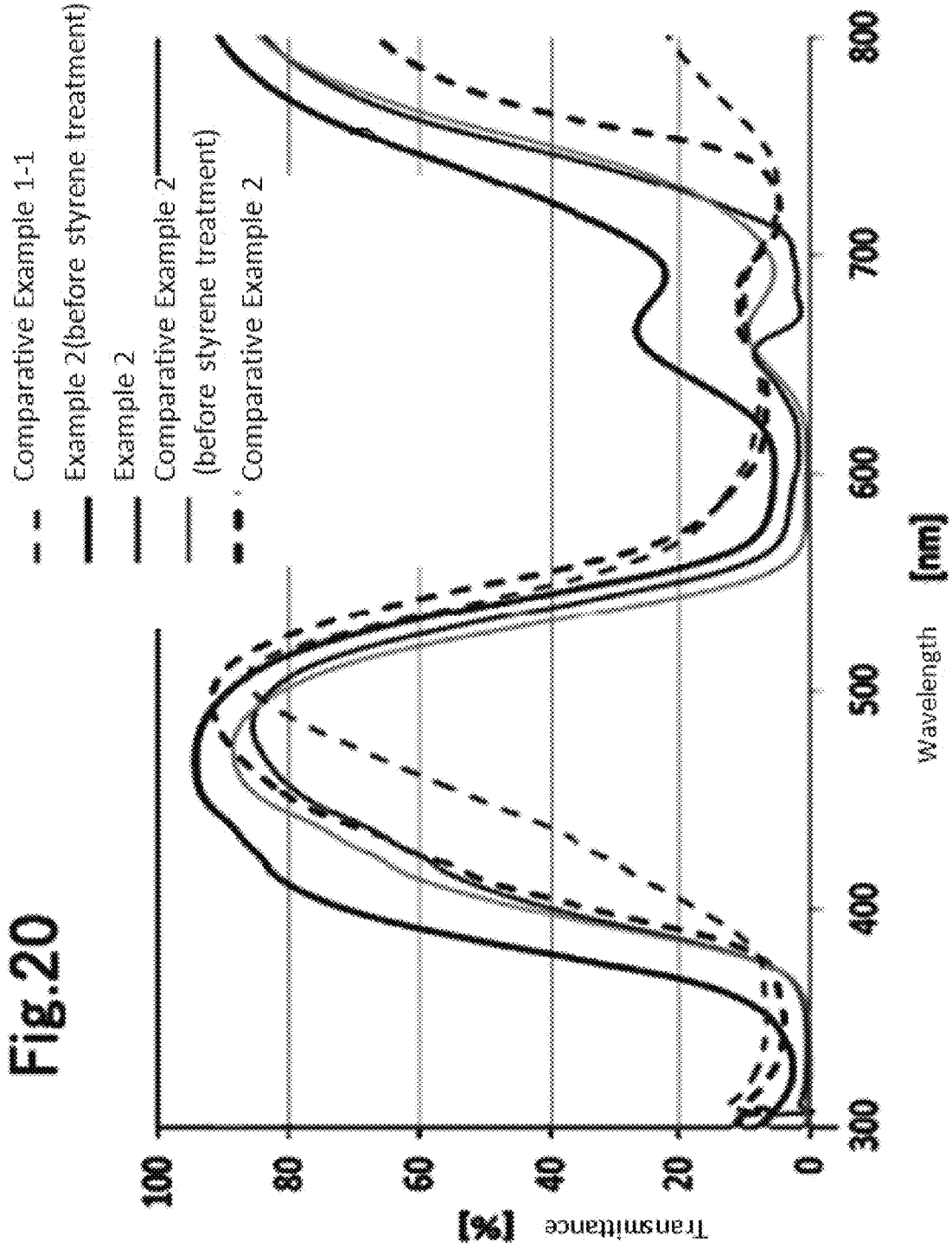

In FIG. 19, the measurement results of the absorption spectra of Example 2 and Comparative Example 2 are shown. Similarly, the measurement results of the transmission spectra of Example 2 and Comparative Example 2 are shown in FIG. 20. Meanwhile, for reference, in both Example 2 and Comparative Example 2, the measurement results of the absorption and transmission spectra of the microparticles before the styrene treatment in the step 3 as well as the absorption and transmission spectra of Comparative Example 1-1 are shown in FIG. 19 or FIG. 20. In Comparative Example 2, the relative value of Abs (a) to Abs (b) ([Abs(a)]/[Abs(b)]) was less than 0.8, wherein Abs (a) is the absorbance value at the peak top in the range of 655 to 700 nm and Abs (b) is the absorbance value at the peak top in the range of 550 to 640 nm.

As can be seen from these results, in Comparative Example 2, $H_2Pc$ shows the absorption in the wavelength range of 600 to 720 nm, but the peak top thereof in the transmission range of about 400 to 550 nm is shifted to the side of a longer wavelength as compared with Example 1 and Example 2; and thus, it is presumed that this has a strong greenish color. That is to say, it can be seen that the copper-titanyl phthalocyanine microparticles of Example 1 and Example 2 can express the characteristics superior not only to the copper-titanyl phthalocyanine microparticles but also to the phthalocyanine not having a metal.

Examples 3-1 to 3-5

(Step 1 and Step 2)

In Examples 3-1 to 3-5, the A solution and the B solution each was prepared and mixed with the production condition 3; and by the way of the poor solvent crystallization method, the composite phthalocyanine microparticles containing CuPc and CoPc, or the composite phthalocyanine microparticles containing CuPc, CoPc, and TiOPc was separated. In Examples 3-1 to 3-5, unlike Examples 1 and 2, by using a beaker as the reaction vessel instead of the micro reactor, the composite phthalocyanine pigment microparticles were separated with the production condition 3 described below.

(Production Condition 3)

A solution: pure water

B solution: in Examples 3-1 to 3-5, respective B1 to B5, which were obtained by dissolving CuPc, CoPc, and TiOPc into concentrated sulfuric acid with the ratios described below were used.

Example 3-1

B1: CuPc/CoPc/98% $H_2SO_4$=2.1/0.9/97 wt % (CuPc/CoPc=70/30=2.33: weight ratio)

Example 3-2

B2: CuPc/TiOPc/CoPc/98% $H_2SO_4$=1.95/0.9/0.15/97 wt % (CuPc/TiOPc/CoPc=65/30/5: weight ratio (CuPc/TiOPc=2.17 and CuPc/CoPc=13.00))

Example 3-3

B3: CuPc/TiOPc/CoPc/98% $H_2SO_4$=1.8/0.9/0.3/97 wt % (CuPc/TiOPc/CoPc=60/30/10: weight ratio (CuPc/TiOPc=2.00 and CuPc/CoPc=6.00))

Example 3-4

B4: CuPc/TiOPc/CoPc/98% $H_2SO_4$=1.95/0.75/0.3/97 wt % (CuPc/TiOPc/CoPc=65/25/10: weight ratio (CuPc/TiOPc=2.60 and CuPc/CoPc=6.50))

Example 3-5

B5: CuPc/TiOPc/CoPc/98% $H_2SO_4$=1.8/0.6/0.6/97 wt % (CuPc/TiOPc/CoPc=60/20/20: weight ratio (CuPc/TiOPc=3.00 and CuPc/CoPc=3.00))

Preparation of B solutions: in Examples 3-1 to 3-5, all the B solutions were prepared in the way as described below.

Clearmix (CLM-2.2S, manufactured by M. Technique co., Ltd.): rotation number of 20000 rpm, preparation time of 30 minutes, and preparation temperature of 30° C. (preparation amount of 470 g=300 cc)

Mixing and separation of microparticles: 30 mL of the B solution was added dropwise into 100 mL of the A solution in a beaker with stirring to separate the composite phthalocyanine microparticles.

(Step 3)

In all of Examples 3-1 to 3-5, the mixed solution of the A solution and the B solution was filtrated in the subsequent step, and then, the obtained composite phthalocyanine microparticles were washed with pure water for three times by using Clearmix. After the obtained wet cake with water was subjected to the solvent substitution with ethanol, the same treatment was conducted by using styrene so as to make styrene act on the composite phthalocyanine microparticles (styrene treatment), thereby the wet cake with styrene was finally obtained. From the wet cake with styrene, dried powder was produced. Part of the obtained wet cake with styrene was diluted with styrene and subjected to the dispersion treatment with styrene to obtain the disperse solution thereof. Preparation methods of each sample for the TEM observation, for the XRD measurement, and for the absorption and transmission spectra as well as the measurement methods of the same were the same as those of Example 1.

The particle diameters of the composite phthalocyanine microparticles obtained in Examples 3-1 to 3-5 were 86.4 nm, 79.4 nm, 87.1 nm, 93.1 nm, and 63.1 nm, respectively; and the aspect ratios of the same were 2.42, 2.41, 2.13, 1.48, and 1.69, respectively.

Figure 11:
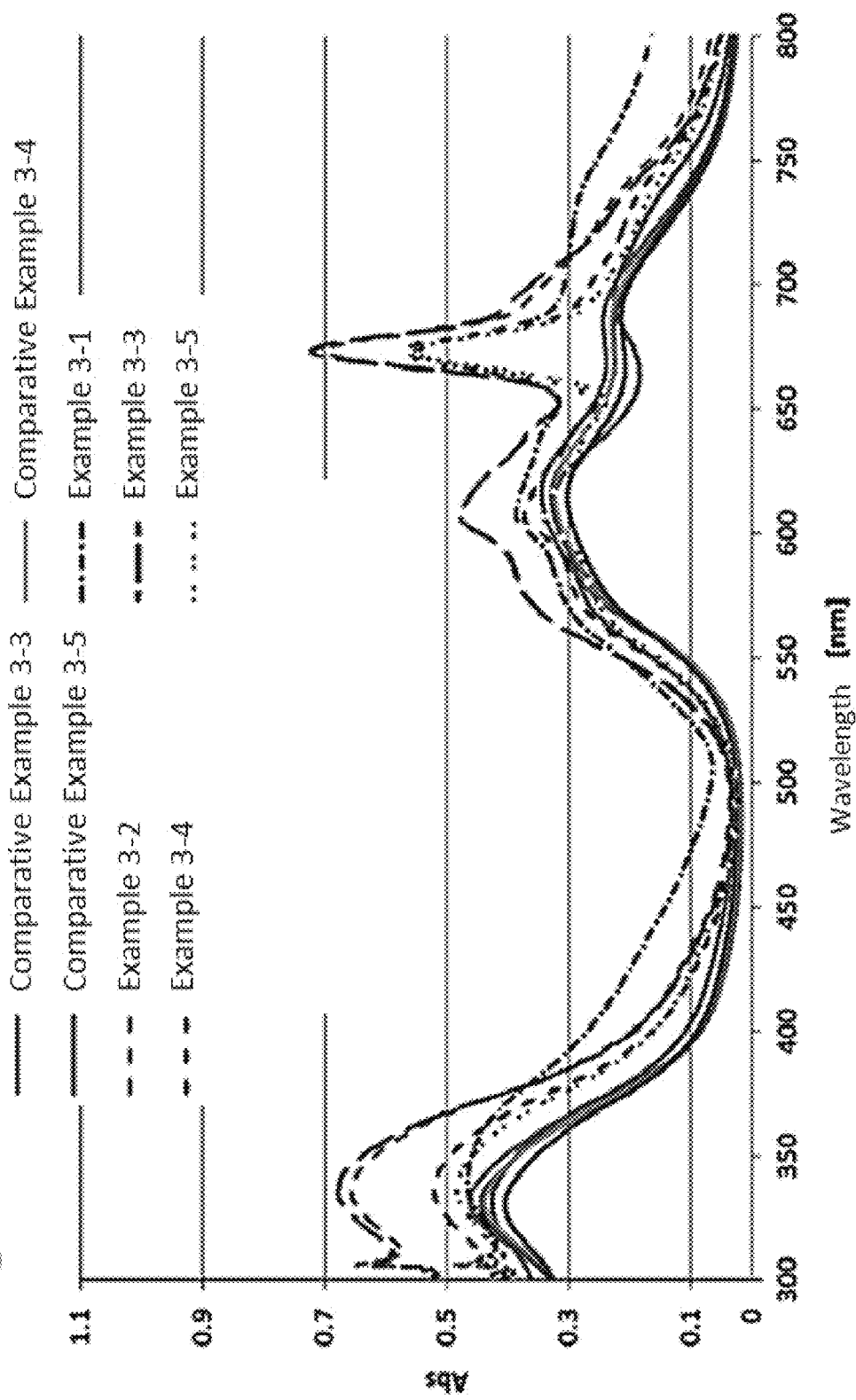
Figure 12:
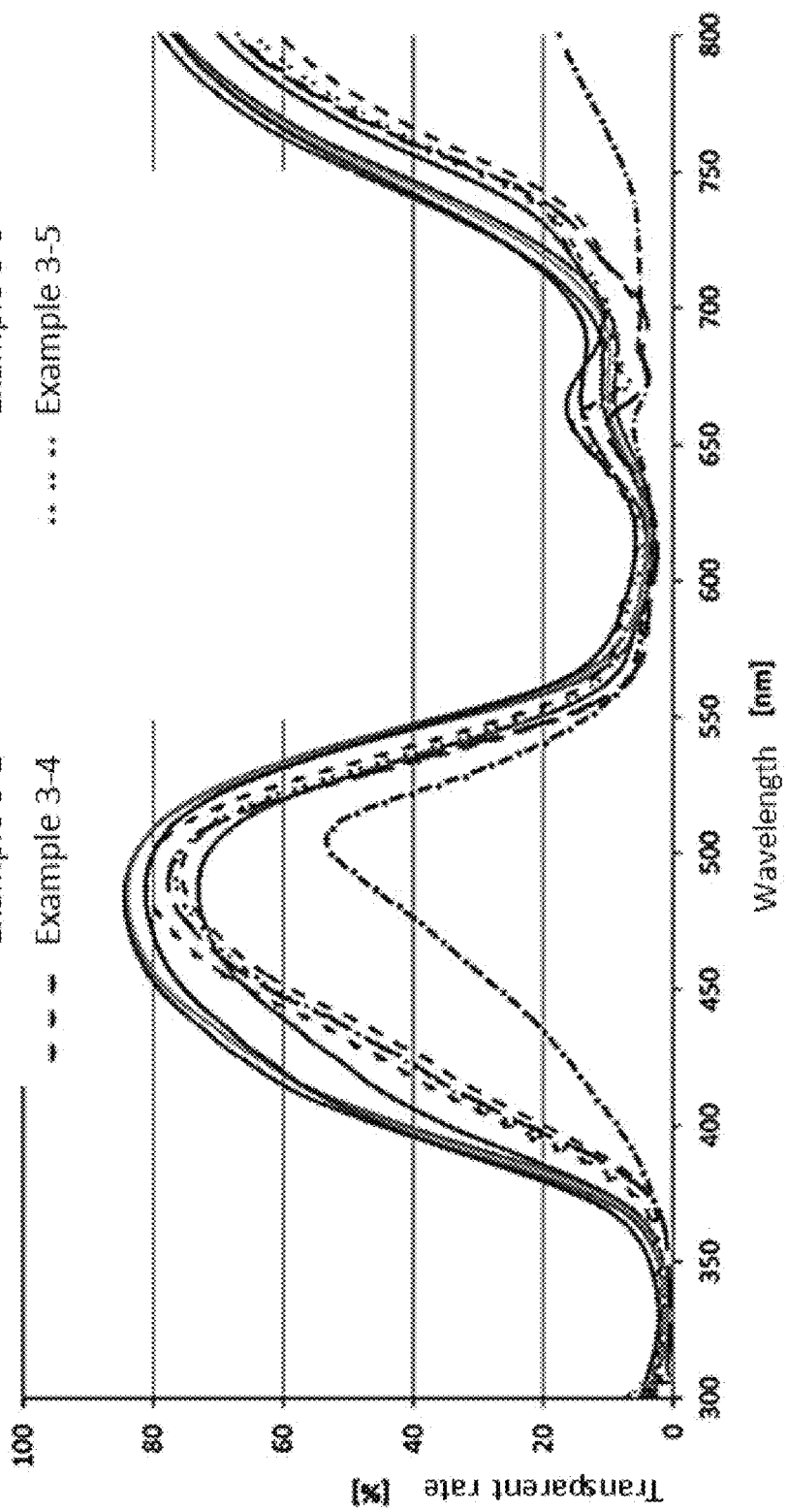

The measurement results of the absorption spectra of Examples 3-1 to 3-5 are shown in FIG. 11 and the measurement results of the transmission spectra of the same are shown in FIG. 12. As the comparative examples to Examples 3-1 to 3-5, similarly to Example 1, the corresponding spectra of the composite phthalocyanine microparticles before the action of styrene in the step 3 of each Example are also shown in FIG. 11 and FIG. 12 as Comparative Examples 3-1 to 3-5. Meanwhile, the particle diameters of the composite phthalocyanine microparticles obtained in Comparative Examples 3-1 to 3-5 were 63.1 nm, 69.3 nm, 61.0 nm, 72.3 nm, and 59.9 nm, respectively; and the aspect ratios of the same were 1.24, 1.12, 1.86, 2.21, and 1.54, respectively. As can be seen in FIG. 11 and FIG. 12, Examples 3-1 to 3-5 shown by the dotted lines gave desirable spectrum shapes as those of Examples 1 and 2 mentioned before. In Examples 3-1 to 3-5, the relative values of Abs (a) to Abs (b) ([Abs(a)]/[Abs(b)]) were 1.45, 1.51, 1.51, 1.51, and 1.46, respectively wherein Abs (a) is the absorbance value at the peak top in the range of 655 to 700 nm and Abs (b) is the absorbance value at the peak top in the range of 550 to 640 nm; in all of Comparative Examples 3-1 to 3-5, the relative values of Abs (a) to Abs (b) ([Abs(a)]/[Abs(b)]) were less than 0.8, wherein Abs (a) is the absorbance value at the peak top in the range of 655 to 700 nm and Abs (b) is the absorbance value at the peak top in the range of 550 to 640 nm. Further, the ratios of the particle diameters after the styrene treatment (particle diameters of Examples 3-1 to 3-5) to the particle diameters before the styrene treatment (particle diameters of Comparative Examples 3-1 to 3-5) were 1.37, 1.15, 1.43, 1.29, and 1.05, respectively, indicating that growth of the particles (crystals) could be suppressed by the styrene treatment.

Next, by using the dried powders obtained in Comparative Examples 3-1 to 3-5 and Examples 3-1 to 3-5, similarly to Example 1, the X-ray diffraction (XRD) measurements of them were conducted. The results of them are shown in FIG. 14 (Comparative Examples 3-1 to 3-5) and in FIG. 15 (Examples 3-1 to 3-5).

Figure 14:
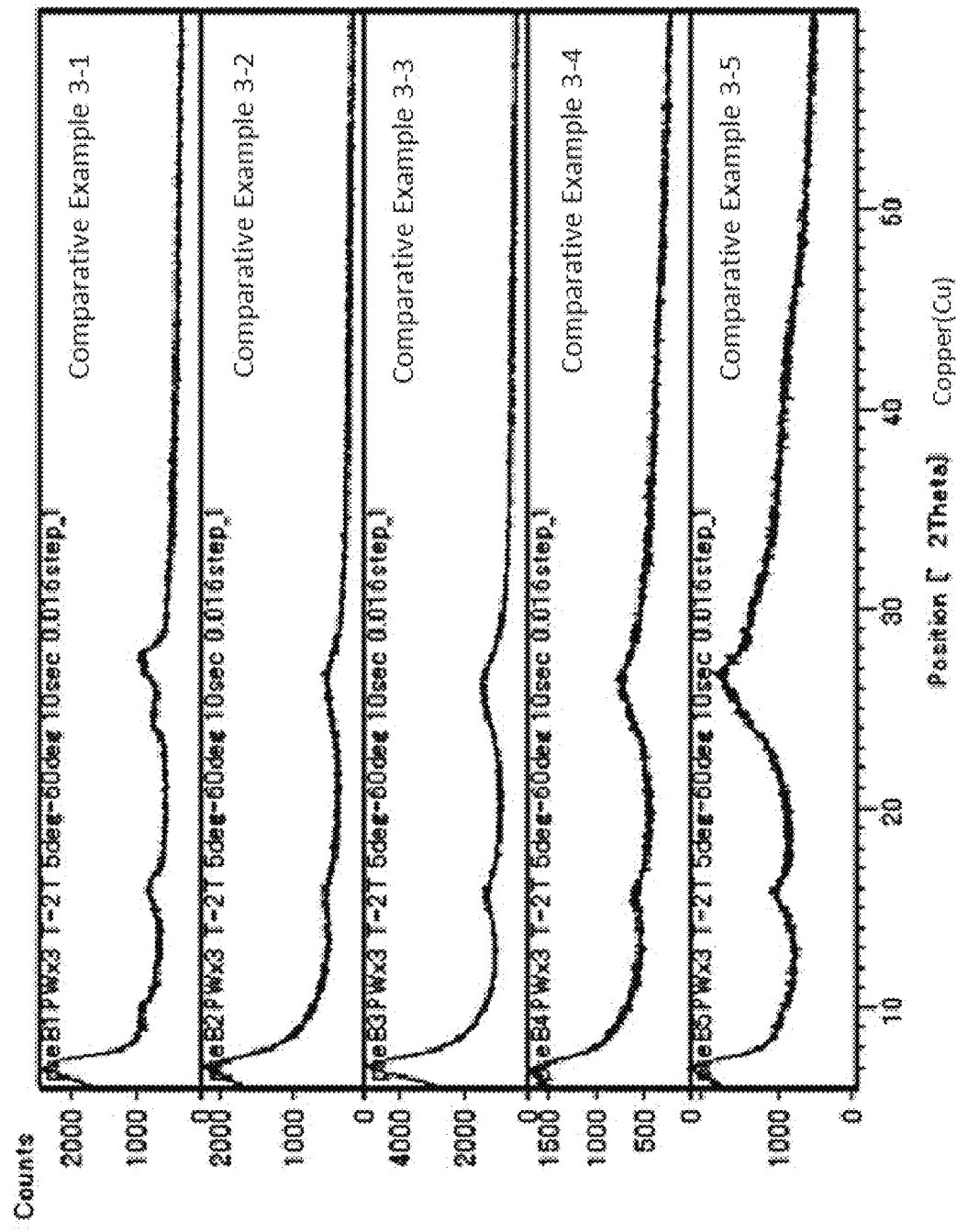
Figure 15:
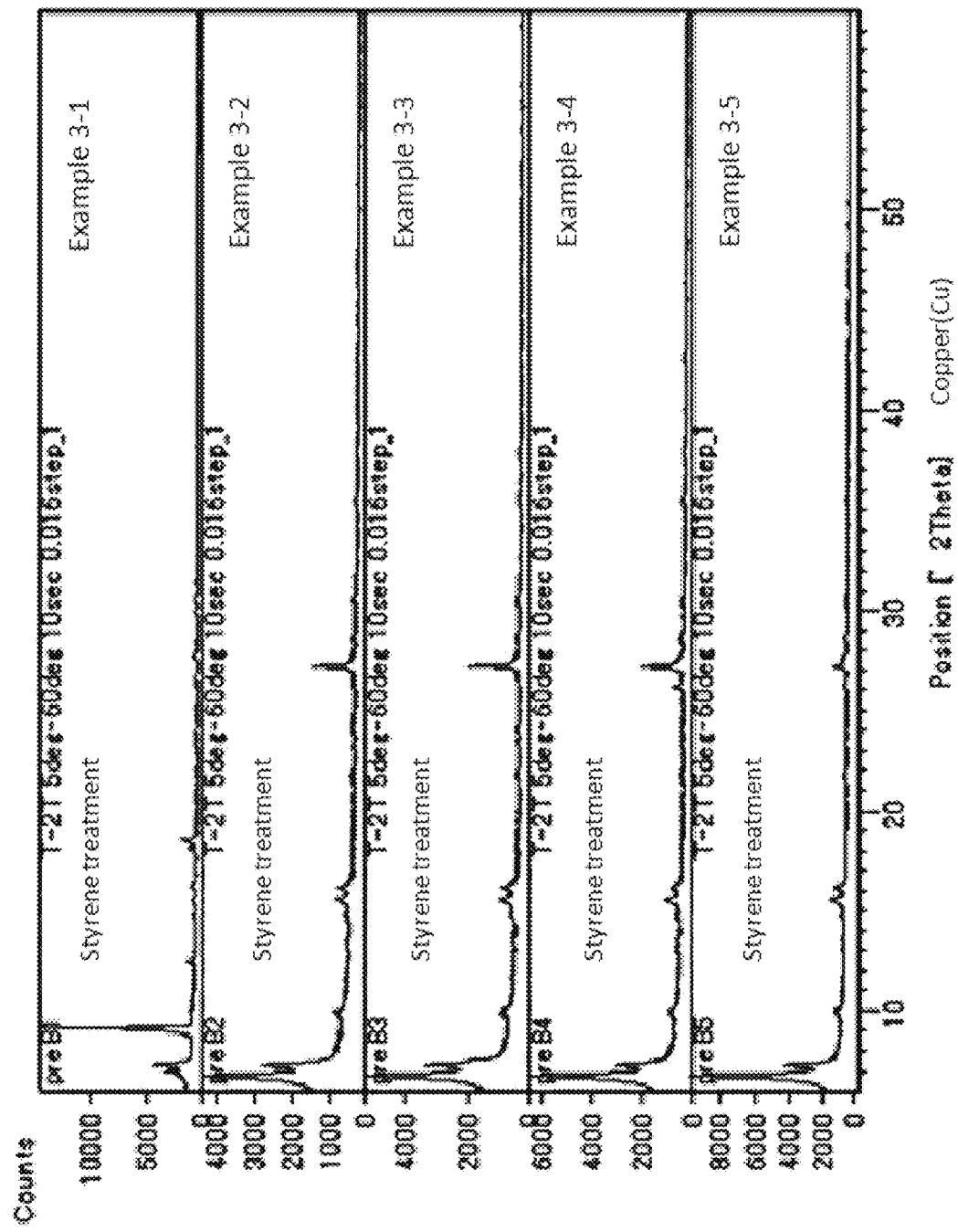

From the results shown in FIG. 14 and FIG. 15, it can be confirmed that although styrene is made to act so as to usually cause the crystal transformation from the alpha-type CuPc to the beta-type CuPc, there is no significant change occurred in the crystal type itself of the composite phthalocyanine microparticles of Examples 3-1 to 3-5 as compared with that of Comparative Examples 3-1 to 3-5.

From the results obtained above, firstly from the result of Example 3-1, it can be understood that in the copper-cobalt phthalocyanine, too, the same effects as those of the copper-titanyl phthalocyanines of Examples 1 and 2 can be obtained. From the results of Examples 3-2 to 3-5, it can be understood that in the composite phthalocyanine of three phthalocyanines, comprising the copper phthalocyanine, the titanyl phthalocyanine, and the cobalt phthalocyanine, too, the same effects as those of the copper-titanyl phthalocyanine or the copper-cobalt phthalocyanine can be obtained.

Examples 3-1-1 to 3-1-3

Hereunder, the cases will be described that the copper-cobalt phthalocyanine microparticles obtained in Example 3-1 were subjected to the actions by organic solvents other than styrene.

Figure 16:
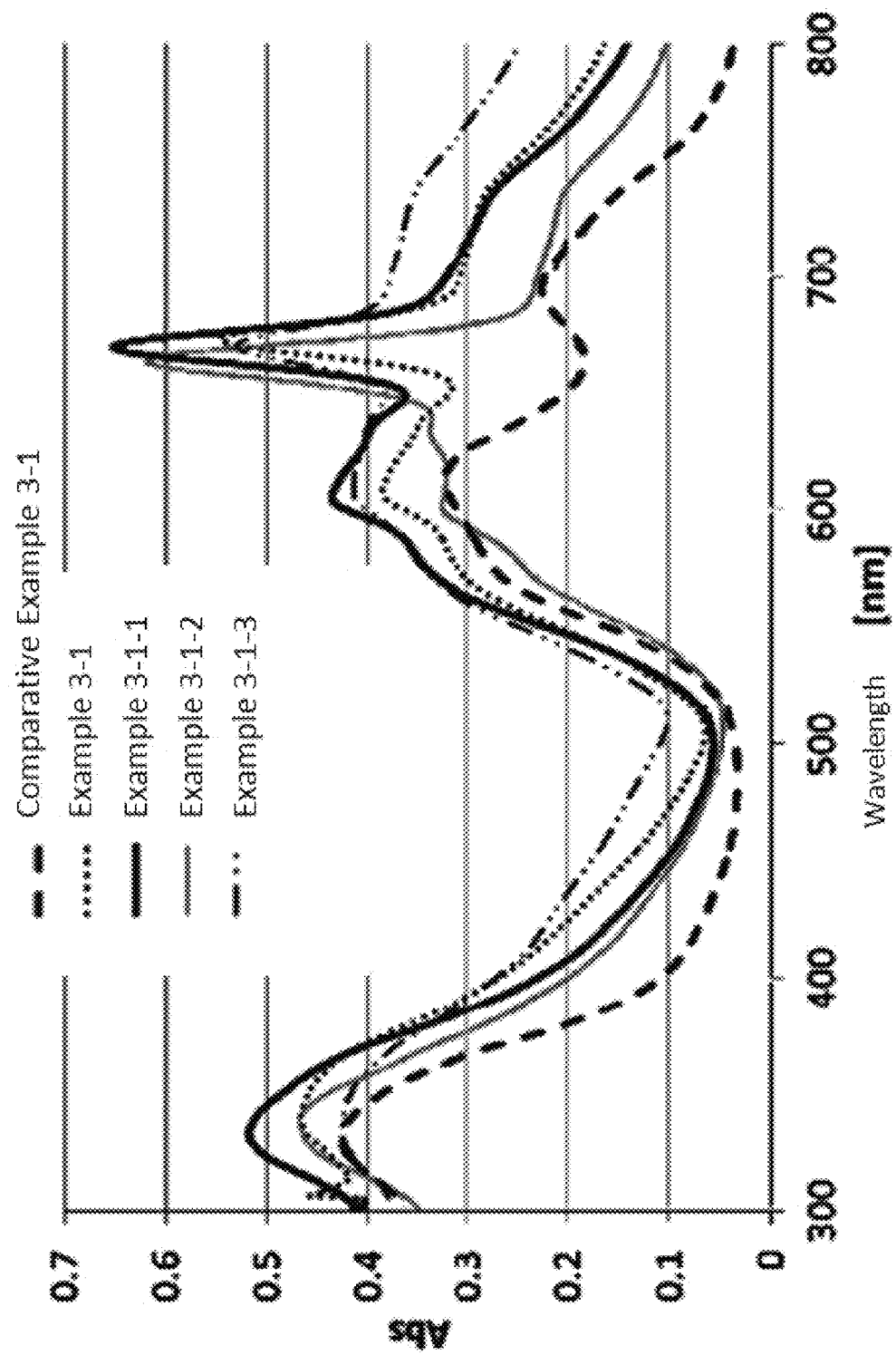

The composite phthalocyanine microparticles were produced in the same way as Example 3-1 except that styrene in Example 3-1 was changed to the organic solvents described below; and then, the absorption spectra thereof were measured. The results of them are shown in FIG. 16, wherein Example 3-1-1 was subjected to the treatment with xylene, Example 3-1-2 was subjected to the treatment with THF, and Example 3-1-3 was subjected to the treatment with toluene. Meanwhile, for reference, the measurement results of the absorption spectra of Example 3-1 and Comparative Example 3-1 are also shown in FIG. 16. From these results, it can be understood that the effects of the present invention can be expressed regardless of the kind of the organic solvent.

Examples 3-2-1 to 3-2-2

Hereunder, the cases will be described that the copper-titanyl-cobalt phthalocyanine microparticles obtained in Example 3-2 were subjected to the actions by organic solvents other than styrene.

The composite phthalocyanine microparticles were produced in the same way as Example 3-2 except that styrene in Example 3-2 was changed to the organic solvents described below; and then, the absorption spectra thereof were measured.

Figure 17:
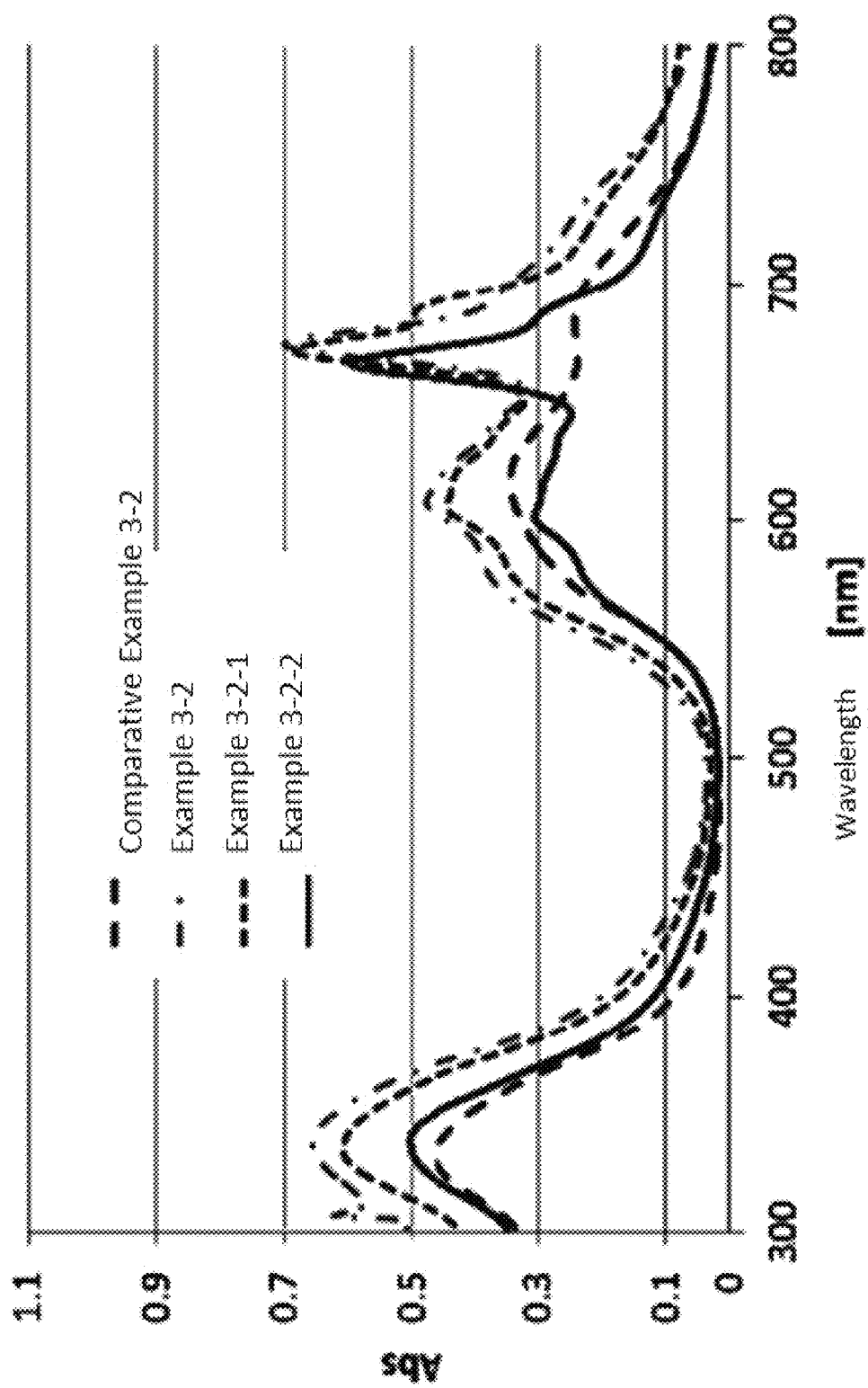

The results of them are shown in FIG. 17, wherein Example 3-2-1 was subjected to the treatment with xylene, and Example 3-2-2 was subjected to the treatment with THF. Meanwhile, for reference, the measurement results of the absorption spectra of Example 3-2 and Comparative Example 3-2 are also shown in FIG. 17. From these results, it can be understood that the effects of the present invention can be expressed regardless of the kind of the organic solvent.

Example 3-3-1

Hereunder, the cases will be described that the copper-titanyl-cobalt phthalocyanine microparticles obtained in Example 3-3 were subjected to the actions by organic solvents other than styrene. Meanwhile, for reference, the measurement results of the absorption spectra of Example 3-3 and Comparative Example 3-3 are also shown. From these results, it can be understood that the effects of the present invention can be expressed regardless of the kind of the organic solvent.

Figure 18:
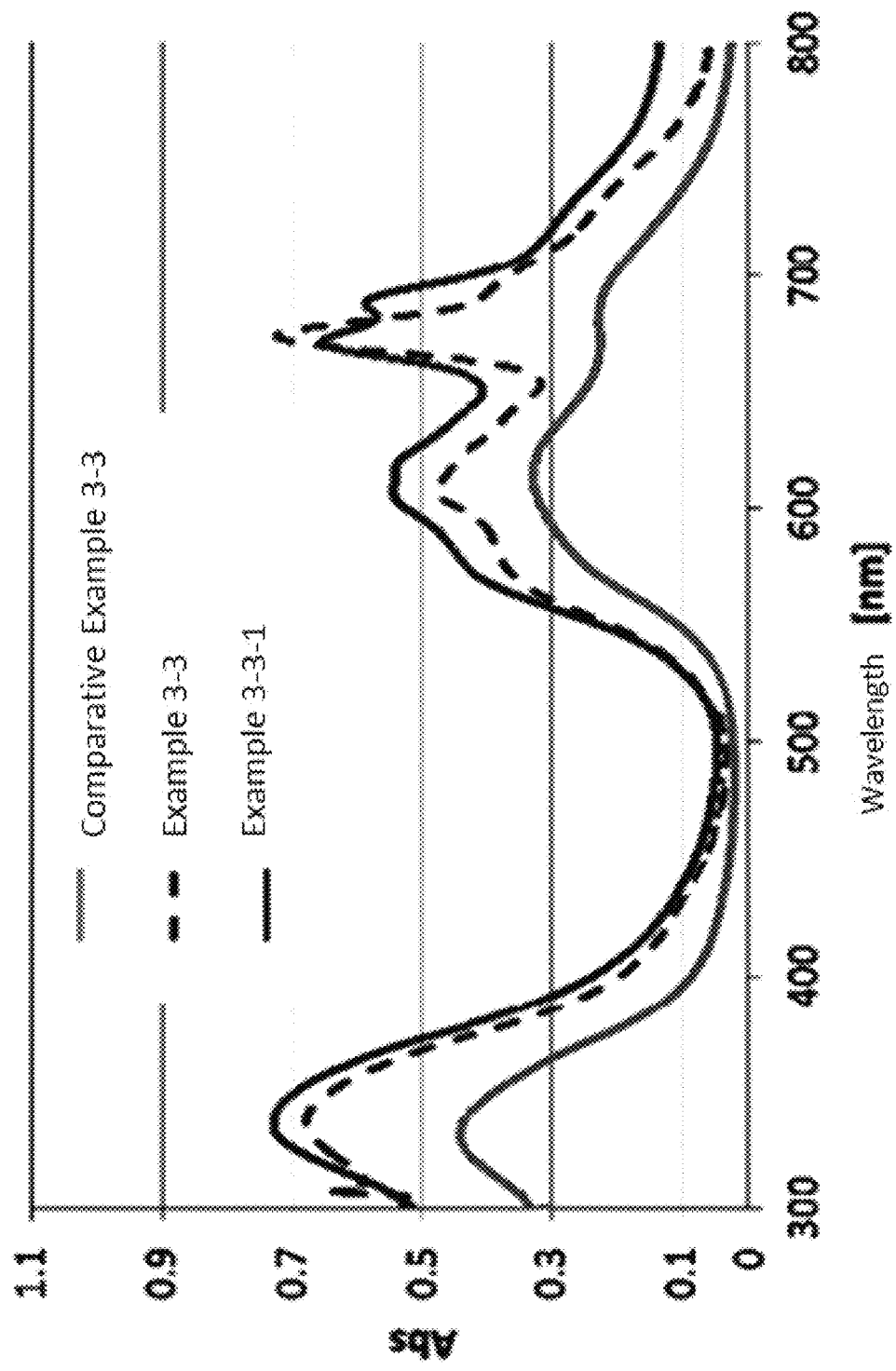

The composite phthalocyanine microparticles were produced in the same way as Example 3-3 except that styrene in Example 3-3 was changed to toluene (Example 3-3-1); and then, the absorption spectrum thereof was measured. This result is shown in FIG. 18.

The particle diameters, aspect ratios, and relative values of Abs (a) to Abs (b) ([Abs(a)]/[Abs(b)]) of Examples 3-1-1 to 3-3-1 are shown in Table 1, wherein Abs (a) is the absorbance value at the peak top in the range of 655 to 700 nm and Abs (b) is the absorbance value at the peak top in the range of 550 to 640 nm.

TABLE 1

| Example | Particle diameter (nm) | Aspect ratio | [Abs(a)]/[Abs(b)] |
|---|---|---|---|
| 3-1-1 | 12.4 | 1.56 | 1.49 |
| 3-1-2 | 25.1 | 1.25 | 1.84 |
| 3-1-3 | 31.4 | 2.13 | 1.32 |
| 3-2-1 | 43.7 | 1.99 | 1.97 |
| 3-2-2 | 33.3 | 1.25 | 1.97 |
| 3-3-1 | 45.9 | 2.12 | 1.22 |

Examples 4-1-1 to 4-1-4 and 4-2-1 to 4-2-4

(Step 1 and Step 2)
Similarly to Examples 1 and 2, by using ULREA SS-11 (manufactured by M. Technique Co., Ltd.) as the micro reactor with the type of a forced thin film, the copper-titanyl-cobalt phthalocyanine microparticles were produced with the production condition 4 described below. Firstly, the copper phthalocyanine, the titanyl phthalocyanine, and the cobalt phthalocyanine were mixed with and dissolved into concentrated sulfuric acid to prepare a dissolved solution of them; and the dissolved solution and a solvent capable of being a poor solvent to the raw materials (pure water) were mixed by using ULREA SS-11 to separate the composite phthalocyanine. The discharged solution containing the composite phthalocyanine microparticles was discharged from between the processing surfaces 1 and 2.

(Production Condition 4)
A solution: pure water
B solution: The solutions obtained by dissolving CuPc, CoPc, and TiOPc into concentrated sulfuric acid with the ratios described below B6 and B7, respectively, were used.

Examples 4-1-1 to 4-1-4

B6: CuPc/TiOPc/CoPc/98% $H_2SO_4$=1.8/0.9/0.3/97 wt % (CuPc/TiOPc/CoPc=60/30/10: weight ratio (CuPc/TiOPc=2.00 and CuPc/CoPc=6.00))

Examples 4-2-1 to 4-2-4

B7: CuPc/TiOPc/CoPc/98% $H_2SO_4$=1.8/0.6/0.6/97 wt % (CuPc/TiOPc/CoPc=60/20/20: weight ratio (CuPc/TiOPc=3.00 and CuPc/CoPc=3.00))
Preparation of B solutions: in Examples 4-1-1 to 4-1-4 and Examples 4-2-1 to 4-2-4, all the B solutions were prepared in the way as described below.
Clearmix (CLM-2.2S, manufactured by M. Technique co., Ltd.): rotation number of 20000 rpm, preparation time of 30 minutes, and preparation temperature of 30° C. (preparation amount of 470 g=300 cc)
ULREA SS-11
   A/B flow rate: 600/30 mL/min
   A/B supply temperature: 10/25° C.
   Disc rotation number: 1700 rpm
(Step 3)
Next, similarly to Examples 1 and 2, the discharged solution was filtrated in the subsequent step to recover the composite phthalocyanine microparticles. The obtained composite phthalocyanine microparticles were washed with pure water for four times by using Clearmix. After the obtained wet cake with water was subjected to the solvent substitution with ethanol, the same treatment was conducted by using styrene (styrene treatment) (Examples 4-1-1 and 4-2-1). Also, in place of the styrene treatment, the same treatments were conducted by using xylene (Examples 4-1-2 and 4-2-2), by using toluene (Examples 4-1-3 and 4-2-3), and by using THF (Examples 4-1-4 and 4-2-4) so as to make the respective solvents act on the composite phthalocyanine microparticles, thereby the wet cakes with the respective solvents were finally obtained. From the obtained wet cakes, dried powders were produced. Part of each of the obtained wet cakes with respective solvents was diluted with the organic solvent which was used for final substitution so as to conduct the dispersion treatment to obtain each of the disperse solutions. Preparation methods of each sample for the TEM observation, for the XRD measurement, and for the absorption and transmission spectra as well as the measurement methods of the same were the same as those of Example 1.

Figure 21:
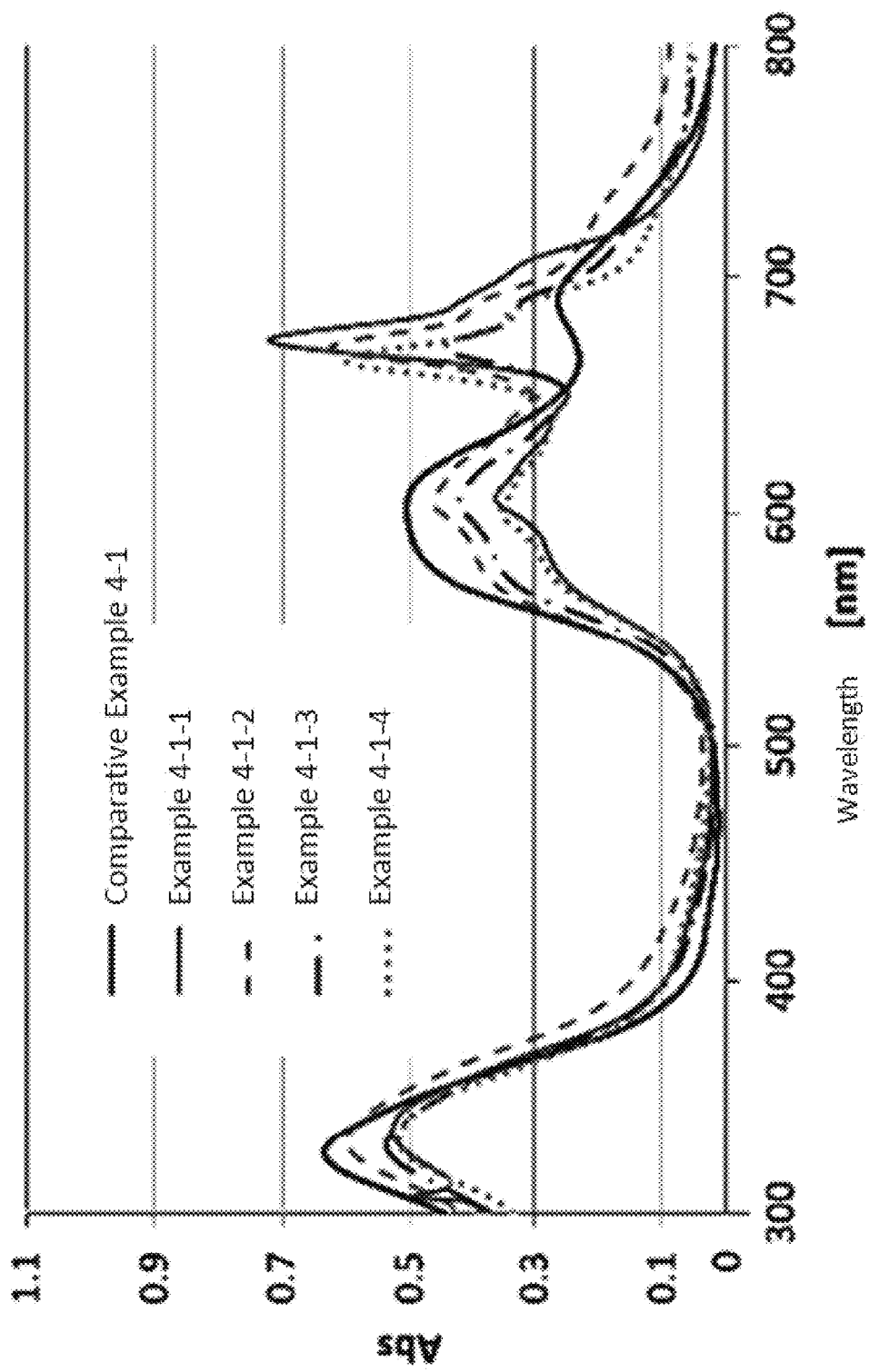
Figure 22:
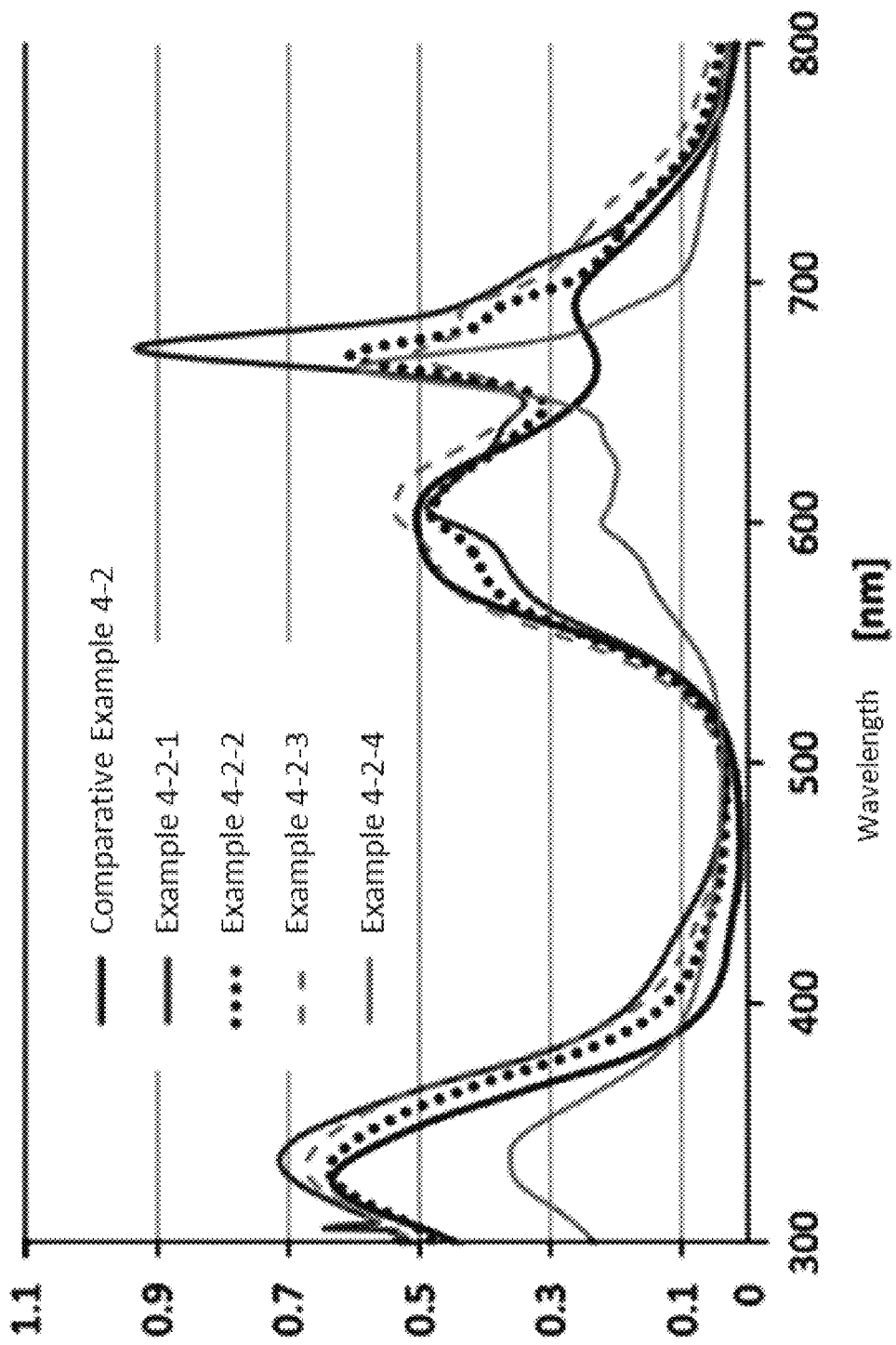

The measurement results of the absorption spectra of Examples 4-1-1 to 4-1-4 are shown in FIG. 21, and the measurement results of the absorption spectra of Examples 4-2-1 to 4-2-4 are shown in FIG. 22. As the comparative example to Examples 4-1-1 to 4-1-4, the measurement result of the absorption spectrum of the composite phthalocyanine microparticles before the action of styrene, xylene, toluene, or THF in the step 3 of each Example is also shown in FIG. 21 (Comparative Example 4-1).

Similarly, as the comparative example to Examples 4-2-1 to 4-2-4, the measurement result of the absorption spectrum of the composite phthalocyanine microparticles before the action of styrene, xylene, toluene, or THF is also shown in FIG. 22 (Comparative Example 4-2).

The particle diameters of the composite phthalocyanine microparticles obtained in the above-mentioned Examples and Comparative Examples were: 11.4 nm in Comparative Example 4-1, 14.6 nm in Example 4-1-1, 23.5 nm in Example 4-1-2, 22.9 nm in Example 4-1-3, and 56.4 nm in Example 4-1-4; and the aspect ratios of the same were 1.19, 2.11, 1.45, 1.54, and 1.78, respectively.

Also the particle diameters thereof were 9.5 nm in Comparative Example 4-2, 13.1 nm in Example 4-2-1, 13.6 nm in Example 4-2-2, 15.4 nm in Example 4-2-3, and 7.4 nm in Example 4-2-4; and the aspect ratios of the same were 1.01, 1.33, 1.29, 2.14, and 2.46, respectively.

The ratios of the particle diameters after the organic solvent treatment (particle diameters of Examples 4-1-1 to 4-1-4) to the particle diameter before the organic solvent treatment (particle diameter of Comparative Examples 4-1) were 1.28, 2.06, 2.01, and 4.95, respectively; and the ratios of the particle diameters after the organic solvent treatment (particle diameters of Examples 4-2-1 to 4-2-4) to the particle diameter before the organic solvent treatment (particle diameter of Comparative Examples 4-2) were 1.38, 1.43, 1.62, and 0.78, respectively; and thus, these indicate that growth of the particles (crystals) could be suppressed by the organic solvent treatment.

As can be seen in FIG. 21, Examples 4-1-1 to 4-1-4 gave desirable spectrum shapes as those of Examples 1 and 2 mentioned before. In Examples 4-1-1 to 4-1-4, the relative values of Abs (a) to Abs (b) ([Abs(a)]/[Abs(b)]) were 1.97, 1.36, 1.07, and 1.72, respectively, wherein Abs (a) is the absorbance value at the peak top in the range of 655 to 700 nm and Abs (b) is the absorbance value at the peak top in the range of 550 to 640 nm; and in Comparative Example 4-1, the relative value of Abs (a) to Abs (b) ([Abs(a)]/[Abs(b)]) was 0.51, wherein Abs (a) is the absorbance value at the peak top in the range of 655 to 700 nm and Abs (b) is the absorbance value at the peak top in the range of 550 to 640 nm.

As can be seen in FIG. 22, Examples 4-2-1 to 4-2-4 gave desirable spectrum shapes as those of Examples 1 and 2 mentioned before. In Examples 4-2-1 to 4-2-4, the relative values of Abs (a) to Abs (b) ([Abs(a)]/[Abs(b)]) were 1.83, 1.24, 0.91, and 2.62, respectively, wherein Abs (a) is the absorbance value at the peak top in the range of 655 to 700 nm and Abs (b) is the absorbance value at the peak top in the range of 550 to 640 nm; and in Comparative Example 4-1, the relative value of Abs (a) to Abs (b) ([Abs(a)]/[Abs(b)]) was 0.52, wherein Abs (a) is the absorbance value at the peak top in the range of 655 to 700 nm and Abs (b) is the absorbance value at the peak top in the range of 550 to 640 nm.

From the above results, it can be seen that the effects of the present invention can also be expressed in the copper-titanyl-cobalt phthalocyanine that is the composite of three phthalocyanines, the copper phthalocyanine, the titanyl phthalocyanine, and the cobalt phthalocyanine.

Figure 23:
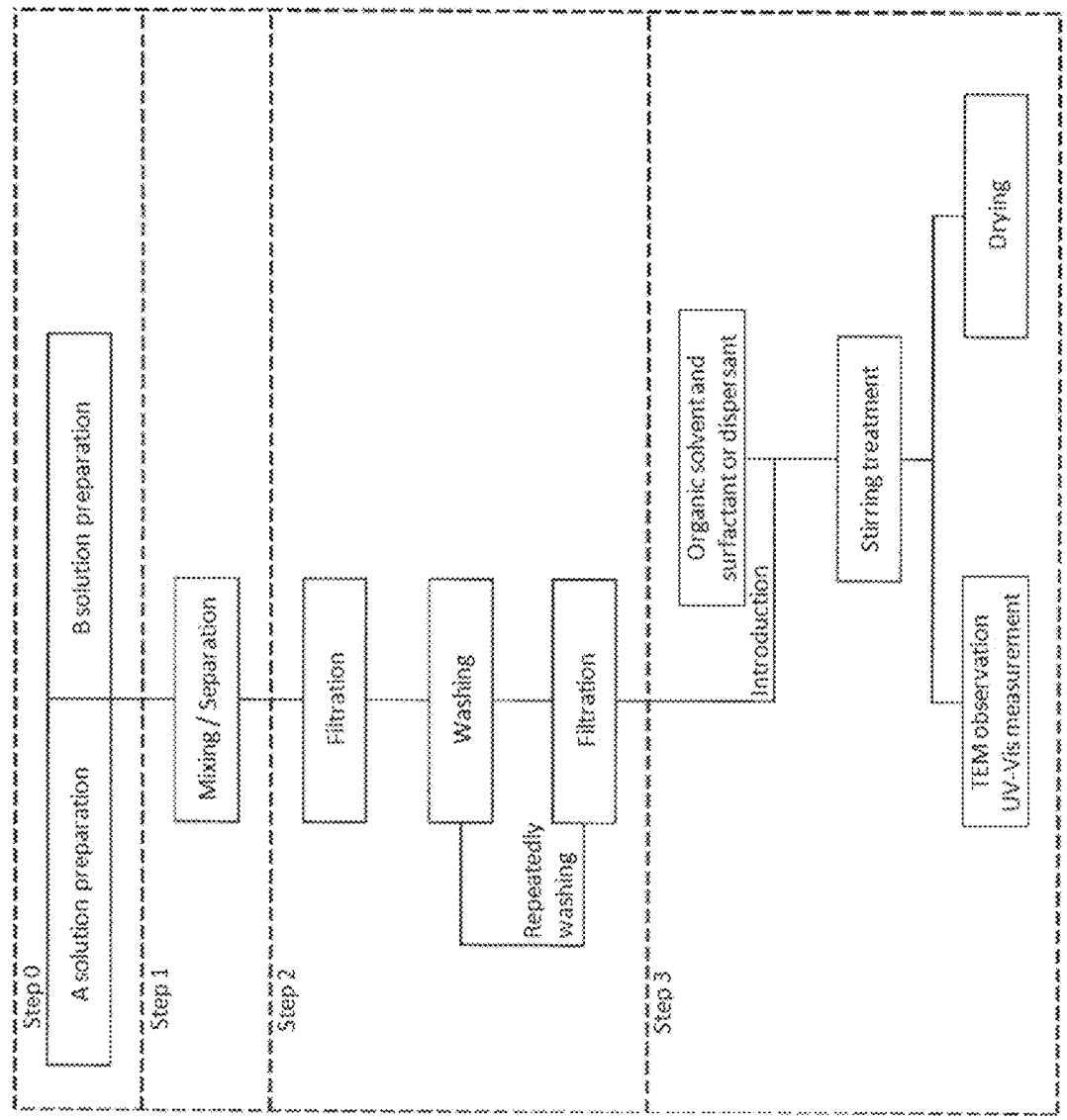
Figure 24:
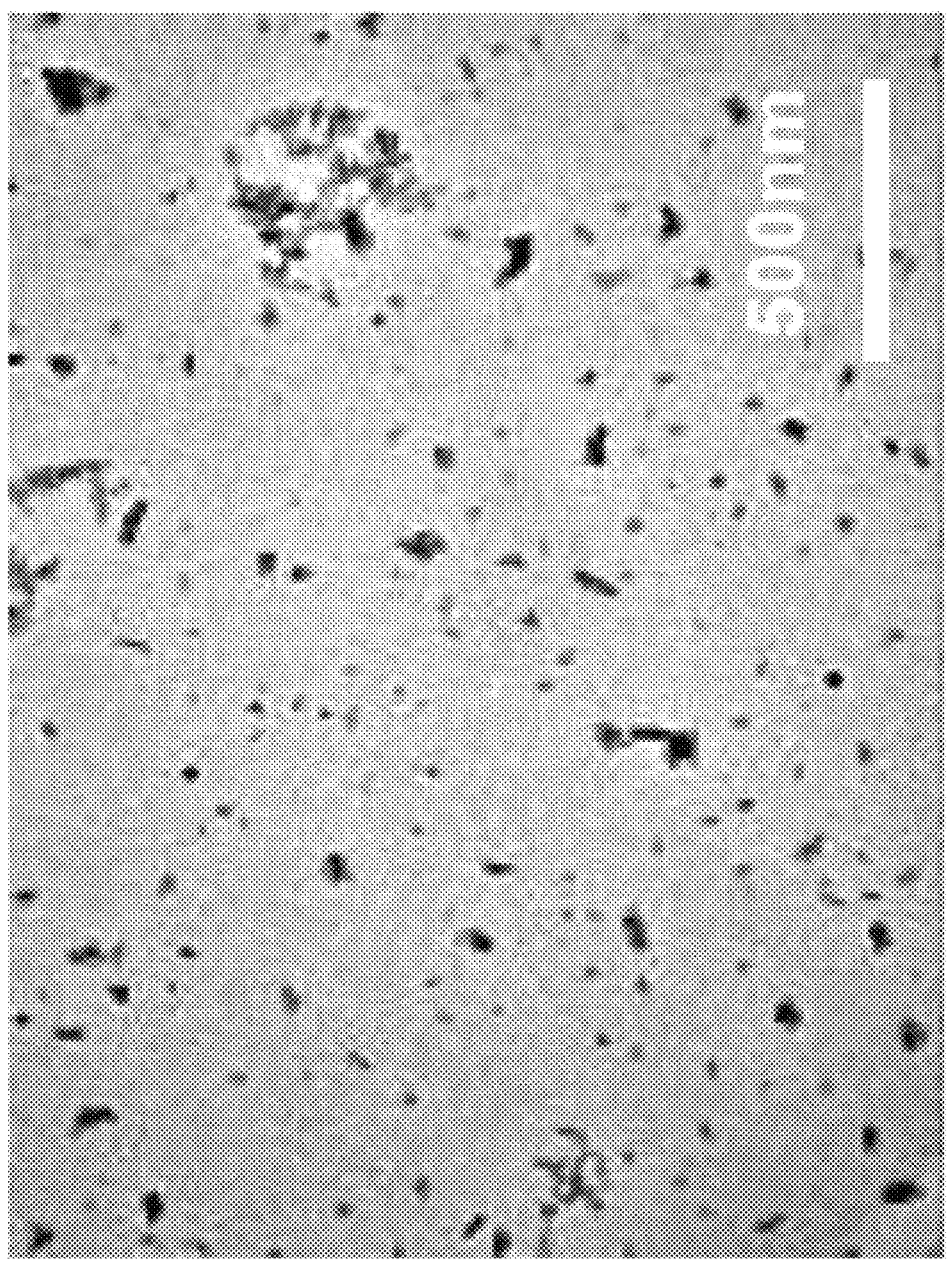
Figure 25:
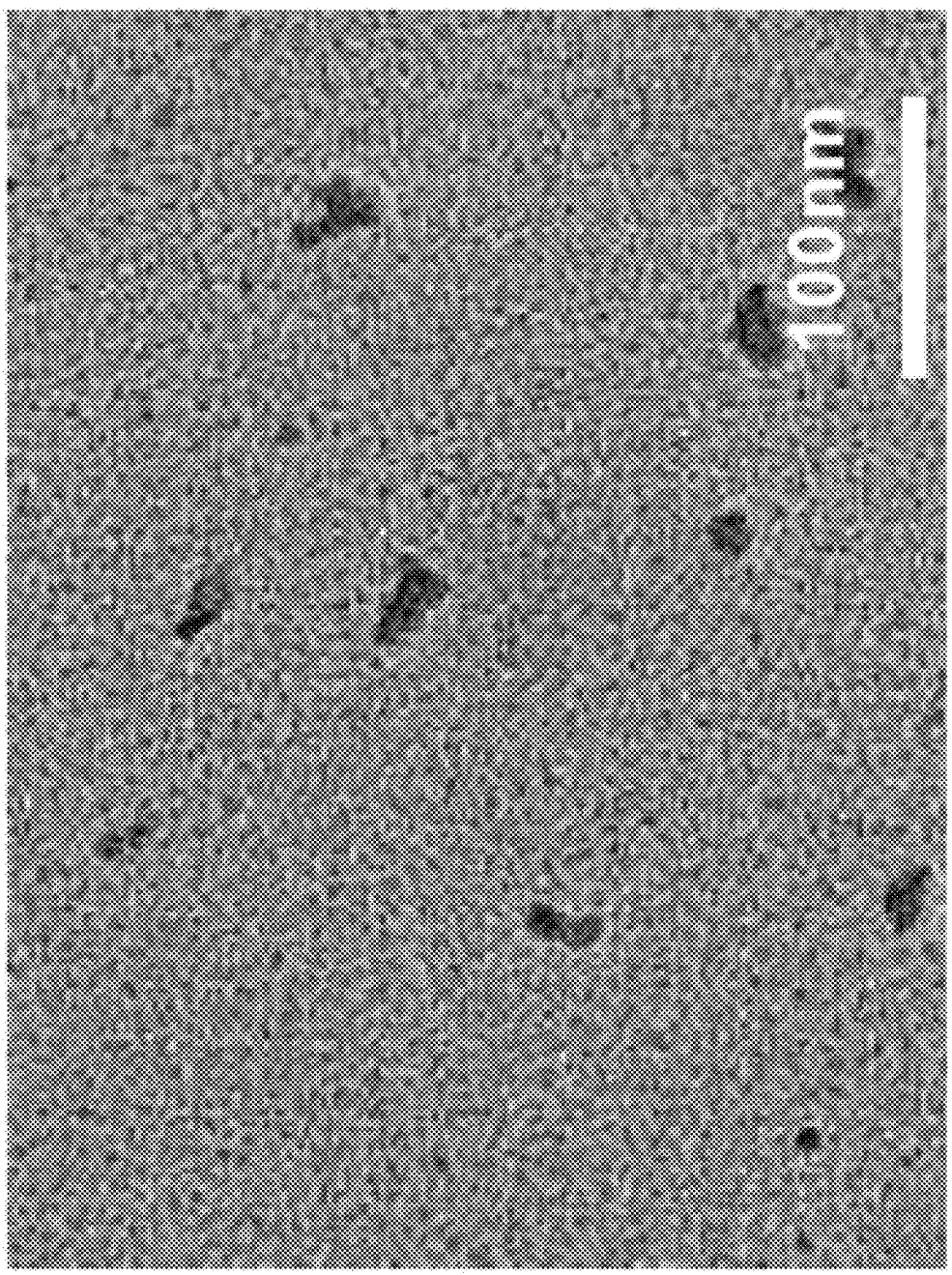
Figure 26:
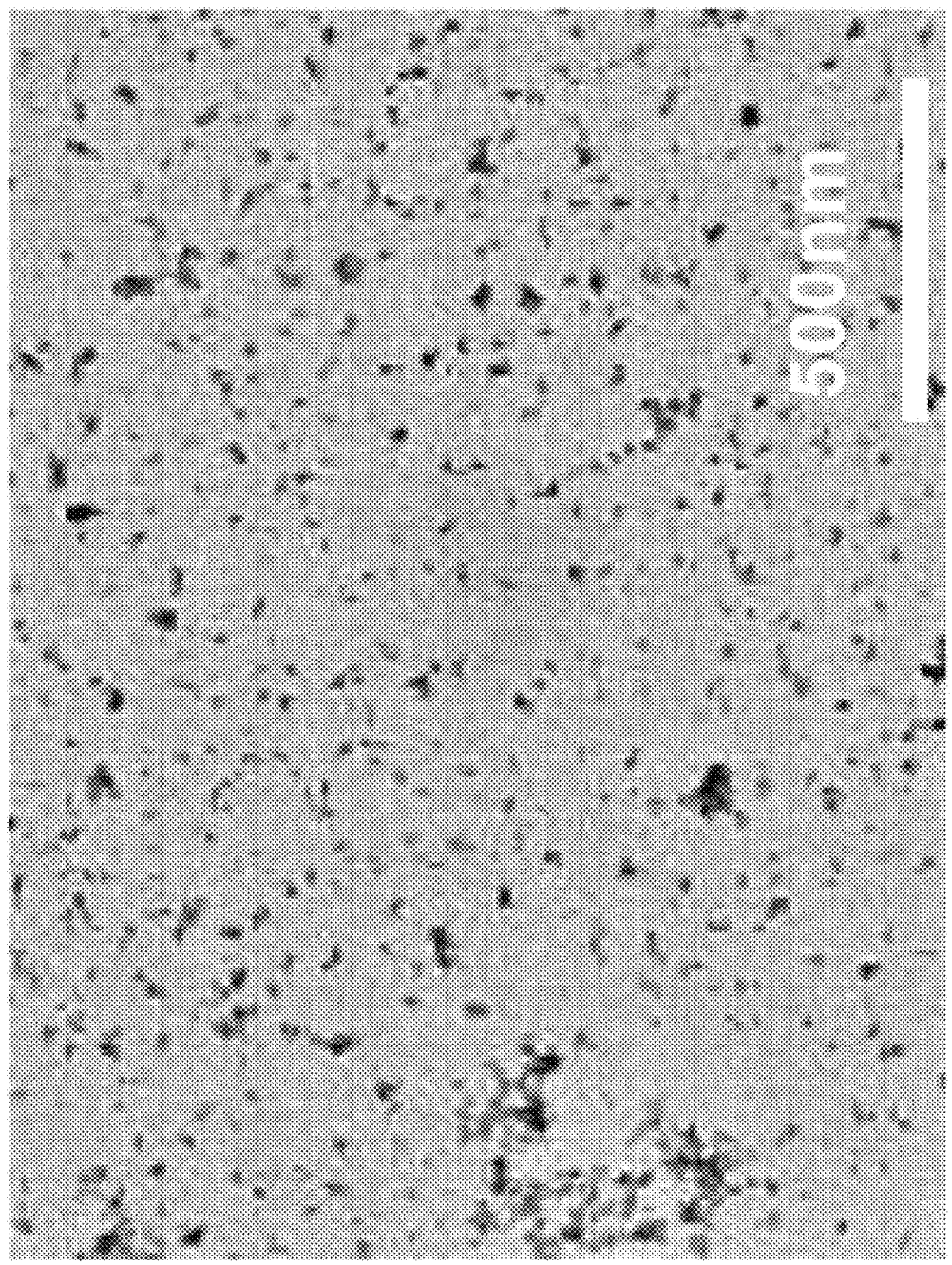
Figure 27:
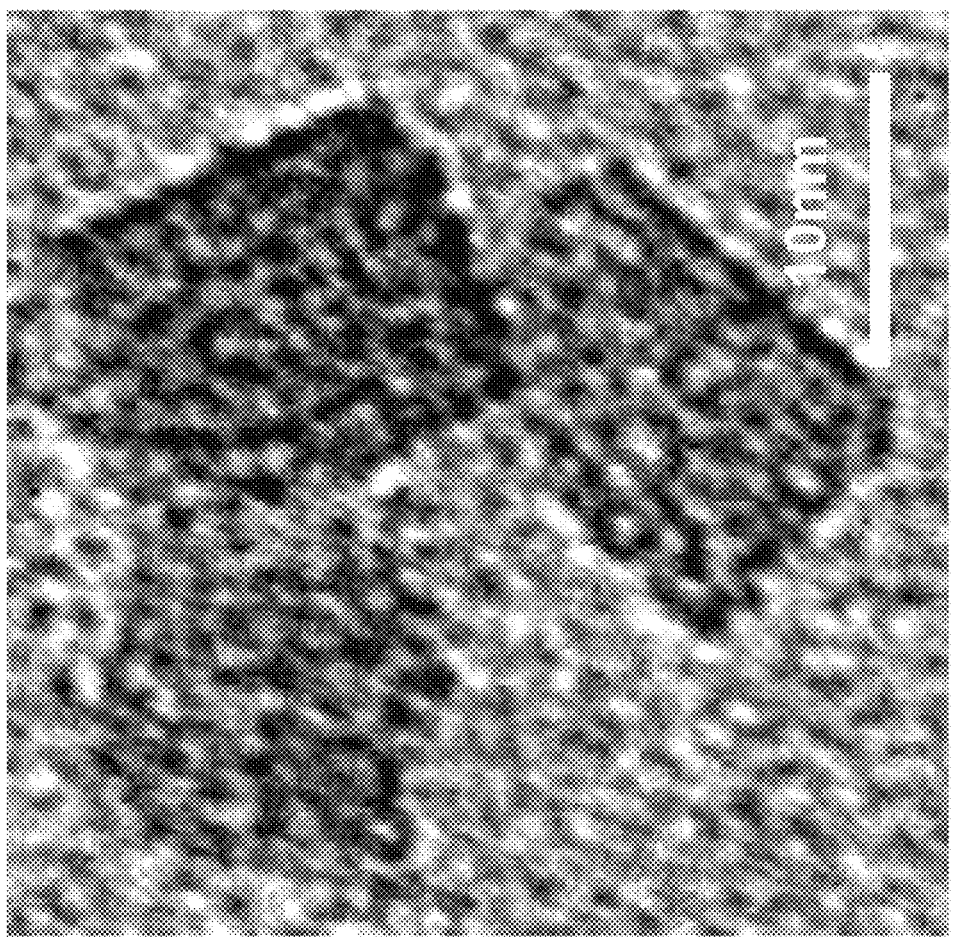

Next, Examples 5 to 8 will be described. Meanwhile, the measurement condition of XRD of Examples 5 to 8 is the same as that of Example 1. The TEM observation was made by using the transmission electron microscope JEM-2100 (manufactured by JEOL Ltd.). The observation conditions were the acceleration voltage of 80 kV and the observation magnification of 25000. In FIG. 23, an example of the production procedure of Examples 5 to 8 is shown.

Examples 5 and 6

By using the micro reactor, the A solution and the B solution were mixed with the condition described below, and the composite phthalocyanine microparticles were produced by the procedure shown in FIG. 23.

Meanwhile, in Examples 5 (Examples 5-1 to 5-6 in Table 4 to be described later) and Examples 6 (Examples 6-1 to 6-6 in Table 4 to be described later), ULREA SS-11 (manufactured by M. Technique Co., Ltd.) was used as the micro reactor. In this case, the A solution corresponds to the first fluid to be processed that is introduced from the first introduction part d1 of the micro reactor shown in FIG. 1(A), and the B solution corresponds to the second fluid to be processed that is introduced from the second introduction part d2 of the same. The first introduction part d1 and the second introduction part d2 are freely interchangeable.

Experimental prescriptions of Examples 5 and 6 are shown in Table 2.

Preparation condition of the raw material solution of the organic pigment particles (B solution):

Stirring was conducted by using CLM-2.2S with the rotation number of 20000 rpm for the period of 30 minutes. The preparation temperatures of both the A solution and the B solution were chosen to be 40° C.

(Step 1)
(Mixing and Separation)

With the operation conditions described in Table 3, by using ULREA SS-11, the solvent for separation of the organic pigment particles (A solution) and the raw material solution of the organic pigment particles (B solution) were mixed to separate the composite phthalocyanine microparticles.

TABLE 3

| | | Supply condition of A solution | | Supply condition of B solution | | Discharged solution | |
|---|---|---|---|---|---|---|---|
| Example | Disk rotation number (rpm) | Flow rate (mL/min) | Temperature (° C.) | Flow rate (mL/min) | Temperature (° C.) | pH | Measurement temperature (° C.) |
| 5-1 to 5-6 | 1700 | 600 | 10.1 | 30 | 40.6 | <1 | 23.1 |
| 6-1 to 6-6 | 1700 | 600 | 10.2 | 30 | 40.1 | <1 | 22.9 |

(Step 2)
(Washing)

The slurry containing the composite phthalocyanine microparticles obtained in the step 1 was filtrated, and then the composite phthalocyanine microparticles were washed with pure water to obtain a wet cake of composite phthalocyanine microparticles (or dried powder of the composite phthalocyanine microparticles by drying treatment thereof by way of a vacuum drying method or the like).

TABLE 2

| | A solution | | | B solution | | |
|---|---|---|---|---|---|---|
| Example | Prescription | pH | Measurement temperature (° C.) | Prescription | pH | Measurement temperature (° C.) |
| 5-1 to 5-6 | Pure water | 6.9 | 13.9 | $CuPc/TiOPc/CoPc/H_2SO_4$ = 2.1/0.6/0.3/97 (weight ratio) | <1 | — |
| 6-1 to 6-6 | Pure water | 6.9 | 13.9 | $CuPc/TiOPc/CoPc/H_2SO_4$ = 2.1/0.45/0.45/97 (weight ratio) | <1 | — |

Contents of each step of Examples 5 and 6 shown in FIG. 23 are as follows.
(Step 0)
(Preparation of A Solution and B Solution)

For mixing and separation with the experimental prescriptions described above by using ULREA SS-11, the A solution and the B solution were prepared in the way as described below. Preparation condition of the solvent for separation of the organic pigment particles (A solution):

As described in the experimental prescriptions above, in the case of a single solvent, preparation thereof is not necessary; however, for example, in the case that the experimental prescription described in the Japanese Patent Laid-Open Publication No. 2009-82902 is used, it is preferable to stir by using Clearmix. For example, in the present Examples, stirring is conducted by using CLM-2.2S with the rotation number of 10000 rpm for the period of 30 minutes.

(Step 3)
(Action)

The wet cake of composite phthalocyanine microparticles (or dried powder) obtained in the step 2 was introduced into a solution obtained by adding a surfactant and/or a dispersant into an organic solvent (in Table 4 shown below, this is described merely as "Solvent"); and after this introduction, the resulting mixture was subjected to the stirring treatment by using Clearmix for a prescribed period. Meanwhile, the organic solvent and the surfactants and/or the dispersants used in Examples 5-1 to 5-6 and Examples 6-1 to 6-6 are shown in Table 4 below.

The changes of the particle diameter of the composite phthalocyanine microparticles before and after the stirring treatment when the micro reactor was used as well as the changes of the crystallinity of the same are shown in Table 4 below.

TABLE 4

| Example | Particle shape after step 2 (washing) Average primary particle diameter: Db (nm) | Crystal type | Step 3 (action) Solvent | Step 3 (action) Surfactant/ dispersant | Step 3 (action) Ratio of surfactant/dispersant to pigment (wt %) | Particle shape after step 3 (action) Average primary particle diameter: Da (nm) | Crystal type | Change of particle diameter before and after the action (Da/Db) | Change of crystallinity before and after the action (Xa/Xb) | Judgement |
|---|---|---|---|---|---|---|---|---|---|---|
| 5-1 | 9.8 | α | Styrene | Pelex TR | 100 | 19.3 | α | 1.97 | 1.19 | ◎ |
| 5-2 | 9.8 | α | Styrene | BYK-2164 | 100 | 11.2 | α | 1.14 | 2.31 | ◎ |
| 5-3 | 9.8 | α | Styrene | BYK-2000 | 100 | 33.1 | α | 3.38 | 2.64 | ◎ |
| 5-4 | 9.8 | α | Styrene | BYK-108 | 100 | 24.1 | α | 2.46 | 2.39 | ◎ |
| 5-5 | 9.8 | α | THF | BYK-2164 | 100 | 21.4 | α | 2.18 | 2.46 | Δ |
| 5-6 | 9.8 | α | IPA | BYK-2001 | 100 | 18.9 | α | 1.93 | 1.49 | ◎ |
| 6-1 | 8.6 | α | Styrene | Pelex TR | 100 | 14.5 | α | 1.69 | 1.46 | ◎ |
| 6-2 | 8.6 | α | Styrene | BYK-2164 | 100 | 16.3 | α | 1.90 | 1.65 | ◎ |
| 6-3 | 8.6 | α | Styrene | BYK-2000 | 100 | 13.2 | α | 1.53 | 1.89 | Δ |
| 6-4 | 8.6 | α | Styrene | BYK-108 | 100 | 10.1 | α | 1.17 | 1.34 | ◎ |
| 6-5 | 8.6 | α | THF | BYK-2164 | 100 | 10.9 | α | 1.27 | 1.39 | ◎ |
| 6-6 | 8.6 | α | IPA | BYK-2001 | 100 | 16.3 | α | 1.90 | 1.41 | ◎ |

Meanwhile, the abbreviations and definitions of the terms used in Table 2 to Table 4 are summarized in Table 5.

TABLE 5

| Abbreviation/Term | Definition |
|---|---|
| THF | Tetrahydrofuran |
| IPA | Isopropyl alcohol |
| $H_2SO_4$ | Sulfuric acid |
| CuPc | Copper phthalocyanine (blue organic pigment) |
| TiOPc | Titanyl phthalocyanine (blue organic pigment) |
| CoPc | Cobalt phthalocyanine (blue organic pigment) |
| SDBS | Sodium dodecylbenzenesulfonate |
| Measurement method of average primary particle diameter | Average particle diameter of 100 particles observed in plural view fields at the time of TEM observation with 25000 magnification. |
| Crystallinity | The ratio of the crystalized component relative to the total of the crystalized and amorphous components obtained by the XRD measurement. Durability to light, heat, humidity, etc. are higher when the pigment crystallinity is higher. |

Definitions of the evaluation results designated by the symbols ◎, ○, and Δ shown in Table 4 before and in Table 7 to be shown later are as follows.

The symbol ◎ is defined as follows:

when Da represents the average particle diameter of primary particles after the action of the step 3 and Db represents the average particle diameter of primary particles after the washing of the step 2, the ratio Da/Db is in the range of 1.0 and 4.0, and when Xa represents the crystallinity of primary particles after the action of the step 3 and Xb represents the crystallinity of primary particles after the washing of the step 2, the ratio Xa/Xb is in the range of 1.05 or more, and Da is in the range of 80 nm or less, and in view of uniformity of the microparticles, at the time of TEM observation of three view fields with 25000 magnification, the particles having the size of more than 8.0 times relative to Db are not found at all among the individual blue pigment microparticles after the action of the step 3.

The symbol ○ is defined as follows:

the ratio Da/Db is in the range of 1.0 to 4.0, and the ratio Xa/Xb is in the range of 1.05 or more, and Da is in the range of more than 80 nm, and in view of uniformity of the microparticles, at the time of TEM observation of three view fields with 25000 magnification, the particles having the size of more than 8.0 times relative to Db are not found at all among the individual blue pigment microparticles after the action of the step 3.

The symbol Δ is defined as follows:

the ratio Da/Db is in the range of 1.0 to 4.0, and the ratio Xa/Xb is in the range of 1.05 or more, and in view of uniformity of the microparticles, at the time of TEM observation of three view fields with 25000 magnification, a maximum of one particle having the size of more than 8.0 times relative to Db is found among the individual blue pigment microparticles after the action of the step 3.

The average primary particle diameter of the composite phthalocyanine microparticles after the step 2 (washing) and after the step 3 (action) each was calculated by way of the TEM observation, and the crystallinity of the same was measured by the XRD measurement; and they were compared (Table 4). In addition, the TEM pictures obtained in the above-mentioned Examples are shown (FIG. 24 to FIG. 27).

From the above-mentioned Examples, it can be seen that when the separated composite phthalocyanine microparticles are subjected to the action of the organic solvent added with a surfactant or a dispersant (step 3), necking and growth can be suppressed.

Examples 7 and 8

The A solution and the B solution were mixed by way of the batch method with the condition described below, followed by the following procedure described in FIG. 23 to produce the composite phthalocyanine microparticles.

The experimental prescriptions of Examples 7 (Examples 7-1 to 7-6 in Table 7 to be described later) and Examples 8 (Examples 8-1 to 8-6 in Table 7 to be described later) are shown in Table 6.

TABLE 6

| | A solution | | | B solution | | |
|---|---|---|---|---|---|---|
| Example | Prescription | pH | Measurement temperature (° C.) | Prescription | pH | Measurement temperature (° C.) |
| 7-1 to 7-6 | Pure water | 6.9 | 13.9 | CuPc/TiOPc/CoPc/$H_2SO_4$ = 2.1/0.6/0.3/97 (weight ratio) | <1 | — |
| 8-1 to 8-6 | Pure water | 6.9 | 13.9 | CuPc/TiOPc/CoPc/$H_2SO_4$ = 2.1/0.45/0.45/97 (weight ratio) | <1 | — |

Contents of each step of Examples 7 and 8 are as follows.

(Step 0)
(Preparation of A Solution and B Solution)

For mixing and separation with the experimental prescriptions described above by way of the batch method, the A solution and the B solution were prepared in the way as described below. Preparation condition of the solvent for separation of the organic pigment particles (A solution):

As described in the experimental prescription, in the case of a single solvent, preparation thereof is not necessary; however, for example, in the case that the experimental prescription described in the Japanese Patent Laid-Open Publication No. 2009-82902 is used, it is preferable to stir by using Clearmix. For example, in the present Examples, stirring is conducted by using CLM-2.2S with the rotation number of 10000 rpm for the period of 30 minutes. Preparation condition of the raw material solution of the organic pigment particles (B solution):

Stirring was conducted by using CLM-2.2S with the rotation number of 20000 rpm for the period of 30 minutes.

The preparation temperatures of both the A solution and the B solution were 40° C.

(Step 1)
(Mixing and Separation)

The raw material solution of the organic pigment particles (B solution) was introduced into the solvent for separation of the organic pigment particles (A solution) with stirring by using a magnetic stirrer and a stirring bar at 300 rpm so as to mix A solution with the B solution thereby effecting separation of the composite phthalocyanine microparticles.

(Step 2)
(Washing)

The slurry containing the composite phthalocyanine microparticles obtained in the step 1 was filtrated, and then the composite phthalocyanine microparticles were washed with pure water to obtain a wet cake of the composite phthalocyanine microparticles (or dried powder of the composite phthalocyanine microparticles by drying treatment thereof by way of a vacuum drying method or the like).

(Step 3)
(Action)

Similarly to Examples 5 and 6, the wet cake of the composite phthalocyanine microparticles (or dried powder) obtained in the step 2 was introduced into a solution obtained by adding a surfactant and/or a dispersant into an organic solvent (in Table 7 shown below, this is described merely as "Solvent"); and after this introduction, the resulting mixture was subjected to the stirring treatment by using Clearmix for a prescribed period. Meanwhile, the organic solvents and the surfactants and/or the dispersants used in Examples 7-1 to 7-6 and Examples 8-1 to 8-6 are shown in Table 7 below.

The changes of the particle diameter of the composite phthalocyanine microparticles before and after the stirring treatment by way of the batch method as well as the changes of the crystallinity of the same are shown in Table 7 below.

TABLE 7

| | Particle shape after step 2 (washing) | | Step 3 (action) | | | Particle shape after step 3 (action) | | Change of particle diameter before and after the action (Da/Db) | Change of crystallinity before and after the action (Xa/Xb) | Judgement |
|---|---|---|---|---|---|---|---|---|---|---|
| Example | Average primary particle diameter: Db (nm) | Crystal type | Solvent | Surfactant/ dispersant | Ratio of surfactant/dispersant to pigment (wt %) | Average primary particle diameter: Da (nm) | Crystal type | | | |
| 7-1 | 79.8 | α | Styrene | Pelex TR | 100 | 169.4 | α | 2.12 | 1.67 | ○ |
| 7-2 | 79.8 | α | Styrene | BYK-2164 | 100 | 174.6 | α | 2.19 | 1.99 | ○ |
| 7-3 | 79.8 | α | Styrene | BYK-2000 | 100 | 169.4 | α | 2.12 | 1.67 | ○ |
| 7-4 | 79.8 | α | Styrene | BYK-108 | 100 | 131.6 | α | 1.65 | 2.31 | ○ |
| 7-5 | 79.8 | α | THF | BYK-2164 | 100 | 246.5 | α | 3.09 | 2.36 | Δ |
| 7-6 | 79.8 | α | IPA | BYK-2001 | 100 | 316.2 | α | 3.96 | 1.69 | ○ |
| 8-1 | 69.7 | α | Styrene | Pelex TR | 100 | 136.4 | α | 1.96 | 1.57 | ○ |
| 8-2 | 69.7 | α | Styrene | BYK-2164 | 100 | 269.4 | α | 3.87 | 1.89 | ○ |
| 8-3 | 69.7 | α | Styrene | BYK-2000 | 100 | 213.4 | α | 3.06 | 2.34 | ○ |
| 8-4 | 69.7 | α | Styrene | BYK-108 | 100 | 276.4 | α | 3.97 | 2.69 | Δ |
| 8-5 | 69.7 | α | THF | BYK-2164 | 100 | 226.4 | α | 3.25 | 3.64 | ○ |
| 8-6 | 69.7 | α | IPA | BYK-2001 | 100 | 276.1 | α | 3.96 | 1.41 | ○ |

The average primary particle diameter of the composite phthalocyanine microparticles after the step 2 (washing) and after the step 3 (action) each was calculated by way of the TEM observation, and the crystallinity of the same was measured by the XRD measurement; and they were compared (Table 7). The meanings of the symbols, abbreviations, and the like are the same as those of the before-mentioned Examples 5 and 6.

From Examples 7 and 8, it can be seen that, similarly to Examples 5 and 6 in which the micro reactor is used, when the separated composite phthalocyanine microparticles are subjected to the action of the organic solvent added with a surfactant or a dispersant (step 3), necking and growth can be suppressed even in the case of the batch method.

Meanwhile, in the case that the micro reactor is used, if the batch method is employed, in any Example, various methods for preparation of the A solution and the B solution in the step 0 may be conceivable. Instead of Clearmix, an ultrasonic homogenizer, an ultrasonic cleaning machine, or a magnetic stirrer with a stirring bar may also be used. As in the cases of Examples described above, only one of the A solution and the B solution may be prepared; or the step 0 may be omitted in both the A solution and the B solution.

With regard to the A solution and the B solution, besides the above-mentioned examples, examples of publicly known mixing and separation methods such as those described in the Japanese Patent Laid-Open Publication No. 2009-82902 may be used.

Further, in place of the stirring treatment of the step 3 in these Examples, not only a simple mixing treatment without stirring but also contact or spray may be allowed.

EXPLANATION OF NUMERAL SYMBOLS

1 First processing surface
2 Second processing surface
10 First processing member
11 First holder
20 Second processing member
21 Second holder
d1 First introduction part
d2 Second introduction part
d20 Opening

The invention claimed is:

1. A composite phthalocyanine microparticle, wherein the composite phthalocyanine microparticle comprises at least copper phthalocyanine and titanyl phthalocyanine and/or cobalt phthalocyanine, the said microparticle having an aspect ratio in a range of 1.1 to 2.5 (both inclusive) and a particle diameter in a range of 5 to 100 nm (both inclusive).

2. The composite phthalocyanine microparticle according to claim 1, wherein a relative value of Abs (a) at the peak top in the range of 655 to 700 nm of an UV-visible absorption spectrum thereof to Abs (b) at the peak top in the range of 550 to 640 nm of the same ([Abs(a)]/[Abs(b)]) is 0.8 or more.

3. The composite phthalocyanine microparticle according to claim 1, wherein the composite phthalocyanine microparticle comprises titanyl phthalocyanine.

* * * * *